United States Patent
Weiskopf et al.

(10) Patent No.: US 10,781,256 B2
(45) Date of Patent: Sep. 22, 2020

(54) ANTI SIRP-α ANTIBODIES AND BI-SPECIFIC MACROPHAGE ENHANCING ANTIBODIES

(71) Applicant: The Board of Trustees of the Leland Stanford Junior University, Stanford, CA (US)

(72) Inventors: Kipp Andrew Weiskopf, Brookline, MA (US); Aaron Michael Ring, New Haven, CT (US); Jens-Peter Volkmer, Menlo Park, CA (US); Irving L. Weissman, Stanford, CA (US); Nan Guo Ring, New Haven, CT (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 262 days.

(21) Appl. No.: 16/030,377

(22) Filed: Jul. 9, 2018

(65) Prior Publication Data
US 2018/0319883 A1 Nov. 8, 2018

Related U.S. Application Data

(63) Continuation of application No. 15/122,560, filed as application No. PCT/US2015/019954 on Mar. 11, 2015, now Pat. No. 10,081,680.

(60) Provisional application No. 61/951,226, filed on Mar. 11, 2014.

(51) Int. Cl.
*A61K 39/395* (2006.01)
*C07K 16/28* (2006.01)
(Continued)

(52) U.S. Cl.
CPC ...... *C07K 16/2803* (2013.01); *A61K 51/1027* (2013.01); *C07K 16/2863* (2013.01);
(Continued)

(58) Field of Classification Search
None
See application file for complete search history.

(56) References Cited

U.S. PATENT DOCUMENTS 8,895,705 B2   11/2014   Medema et al.
9,334,515 B2    5/2016   Graham et al.
(Continued)

FOREIGN PATENT DOCUMENTS

CN    101880324 B    10/2012
JP    2011518824 A    6/2011
(Continued)

OTHER PUBLICATIONS

Zhang et al., SIRP/CD47 signaling in neurological disorder, Brain Res. 1623:74-80, 2015.*
(Continued)

*Primary Examiner* — Claire Kaufman
(74) *Attorney, Agent, or Firm* — Pamela J. Sherwood; Bozicevic, Field & Francis LLP

(57) ABSTRACT

Anti-SIRPα antibodies, including multi-specific anti-SIRPα antibodies, are provided, as are related compositions and methods. The antibodies of the disclosure bind to SIRPα and can block the interaction of CD47 on one cell with SIRPα on a phagocytic cell. Antibodies that are bispecific for SIRPα and a second antigen are termed Bi-specific Macrophage Enhancing (BiME) antibodies and have emergent properties. The subject anti-SIRPα antibodies find use in various therapeutic methods. Embodiments of the disclosure include isolated antibodies and derivatives and fragments thereof, pharmaceutical formulations comprising one or more of the anti-SIRPα antibodies; and cell lines that produce the antibodies. Also provided are amino acid sequences of exemplary anti-SIRPα antibodies.

14 Claims, 10 Drawing Sheets
(7 of 10 Drawing Sheet(s) Filed in Color)
Specification includes a Sequence Listing.

(51) Int. Cl.
C07K 16/32 (2006.01)
A61K 51/10 (2006.01)
G01N 33/577 (2006.01)
G01N 33/68 (2006.01)
A61K 39/00 (2006.01)

(52) U.S. Cl.
CPC ...... C07K 16/2875 (2013.01); C07K 16/2887 (2013.01); C07K 16/32 (2013.01); G01N 33/577 (2013.01); G01N 33/6854 (2013.01); A61K 2039/505 (2013.01); A61K 2039/507 (2013.01); C07K 2317/24 (2013.01); C07K 2317/31 (2013.01); C07K 2317/51 (2013.01); C07K 2317/515 (2013.01); C07K 2317/565 (2013.01); C07K 2317/64 (2013.01); C07K 2317/732 (2013.01); C07K 2317/76 (2013.01); C07K 2317/92 (2013.01); G01N 2333/70503 (2013.01)

(56) References Cited

U.S. PATENT DOCUMENTS

| 9,352,037 | B2 | 5/2016 | van den Berg |
| 2002/0106369 | A1 | 8/2002 | Horvath et al. |
| 2004/0213792 | A1 | 10/2004 | Clemmons et al. |
| 2005/0058640 | A1 | 3/2005 | Kerschbaumer et al. |
| 2011/0296543 | A1 | 12/2011 | Chang et al. |
| 2013/0022623 | A1 | 1/2013 | Karsunky et al. |
| 2013/0189253 | A1 | 7/2013 | Danska et al. |

FOREIGN PATENT DOCUMENTS

| WO | 2009/021026 A1 | 2/2009 |
| WO | 2009/091547 A1 | 7/2009 |
| WO | 2009/091601 A1 | 7/2009 |
| WO | 2011/034969 A1 | 3/2011 |
| WO | 2013/056352 A1 | 4/2013 |

OTHER PUBLICATIONS

Szilagyi et al., Deffective signal regulatory protein alpha (SIRPA) signaling reduces atherosclerosis in mice, Atherosclerosis, 235: e84-e191, Abstract EAS-0279, 2014, only p. e91 supplied.* Abe et al., "Blocking CD47-SIPRAa Signaling Promotes the Phagocytic Activity of Macrophages Against Hepatocellular Carcinoma", Am. J. Transplant., Apr. 1, 2013, p. 375, vol. 13, Suppl. 5, (Abstract# C1162), Wiley, Hoboken, NJ. Alinari et al.,"Aiemtuzumab (Campath-1H) in the treatment of chronic lymphocytic leukemia", Oncogene, 2007, pp. 3644-3653, 26, Nature Publishing Group, London, United Kingdom. Burger et al., "Phase II Trial of Bevacizumab in Persistent or Recurrent Epithelial Ovarian Cancer or PrimaryPeritoneal Cancer: A Gynecologic Oncology Group Study", Journal of Clinical Oncology, Nov. 20, 2007, pp. 5165-5172, vol. 25, No. 33, American Society of Clinical Oncology, Alexandria, VA. Chen et al., "Enhancement and destruction of antibody function by somatic mutation: unequal occurrence is controlled by V genecombinatorial association", EMBO J., Jun. 1995, pp. 2784-2794, vol. 14, Issue 12, Wiley, Hoboken, NJ. Clynes et al., "Inhibitory Fe receptors modulate in vivo cytoxicity against tumor targets", Nature Medicine, Apr. 2000, pp. 443-446, vol. 6, No. 4, Nature Publishing Group, London, United Kingdom.
Forty Seven, Inc., Petition for Inter Partes Review of U.S. Pat. No. 9,352,037, Filed: Aug. 5, 2016, Case No. IPR2016-01529, 74 Pages.
Forty Seven, Inc., Petition for Inter Partes Review of U.S. Pat. No. 9,352,037, Filed: Aug. 8, 2016, Case No. IPR2016-01530, 76 Pages.
Imai et al., "Comparing antibody and small-molecule therapies for cancer", Nature Reviews/Cancer, Sep. 2006, pp. 714-727, vol. 6, Nature Publishing Group, London, United Kingdom.

Irandoust et al., "Engagement of SIRPa inhibits growth and induces programmed cell death in acute myeloidleukemia cells", PLoS One, Jan. 8, 2013, pp. 1-13, vol. 8, No. 1, e52143, PLOS ONE, San Francisco, CA.
Kim et al., "Antibody Engineering for the Development of Therapeutic Antibodies", Molecules and Cells, Aug. 18, 2005, pp. 17-29, vol. 20, No. 1, Korean Society for Molecular and Cellular Biology, Seoul, Korea.
Lamminmaki et al., "Crystal structure of a recombinant anti-estradiol Fab fragment in complex with the 17ß-estradiol", J. Bioi.Chem., Jul. 12, 2001, pp. 36687-36694,2001, 276, The American Society for Biochemistry and Molecular Biology, Inc., Rockville, MD.
Liu et al., "Signal regulatory protein (SIRPa), a cellular ligand for CD47, regulates neutrophil transmigration", J Biol Chem., Jan. 15, 2002, vol. 277, No. 12, The American Society for Biochemistry and Molecular Biology, Inc., Rockville, MD.
MacCallum et al., "Antibody-antigen interactions:contact analysis and binding site topography", J. Mol. Bioi., Oct. 11, 1996, pp. 732-745, vol. 262, Issue 5, Elsevier, New York City, NY.
Majeti et al., "CD47 is an adverse prognostic factor and therapeutic antibody target on human acute myeloidleukemia stem cells", Cell, Jul. 24, 2009, pp. 286-299, vol. 138, No. 2, Elsevier Inc., Amsterdam, Netherlands.
Mawby et al., "Isolation and characterization of CD47 glycoprotein: a multispanning membrane protein which is thesame as integrin-associated protein (IAP) and the ovarian tumour marker OA3", Biochem. J., 1994, pp. 525-530, 304, Portland Press Limited, London, United Kingdom.
Musolino et al., "Immunoglobulin G Fragment C Receptor Polymorphisms and Clinical Efficacy of Trastuzumab-Based Therapy in Patients With HER-2/neu-Positive Metastatic Breast Cancer", Journal of Clinical Oncology, Apr. 10, 2008, pp. 1789-1796, vol. 26, No. 11, American Society of Clinical Oncology, Alexandria, VA.
Okazawa et al., "Negative Regulation of Phagocytosis in Macrophages by the CD47-SHPS-1 System", The Journal of Immunology, 2005, pp. 2004-2011, 174, The American Association of Immunologists, Inc., Bethesda, MD.
Ojzols, "Challenges for chemotherapy in ovarian cancer", Annals of Oncology, May 2006, pp. v181-v187, vol. 17, Supplement 5, European Society for Medical Oncology, Lugano, Switzerland.
Oldenborg et al., "CD47-Signal Regulatory Protein a (SIRPa) Regulates Fey and Complement Receptor-mediated Phagocytosis", J. Exp. Med., Apr. 12, 2001, pp. 855-861, vol. 193, No. 7, The Rockefeller University Press, New York, NY.
Tanaka et al., "Inhibition of Src homology 2 domain-containing protein tyrosine phosphatase substrate-1 reduces the severity of collagen-induced arthritis", J Rheumatol., Nov. 1, 2008, pp. 2316-2324, vol. 35, No. 12, The Journal of Rheumatology, Toronto, ON Canada.
Tibes et al., "Activity of Alemtuzumab in Patients with CD52-Positive Acute Leukemia", Cancer, Jun. 15, 2006, pp. 2645-2651, vol. 106, No. 12, American Cancer Society, Atlanta, GA.
Veillette et al., "High Expression of Inhibitory Receptor SHPS-1 and Its Association with Protein-tyrosine Phosphatase SHP-1 in Macrophages", The Journal of Biological Chemistry, Aug. 28, 1998, pp. 22719-22728, vol. 273, No. 35, The American Society for Biochemistry and Molecular Biology, Inc., Rockville, MD.
Weiskopf et al., "Engineered SIRP Variants as Immunotherapeutic Adjuvants to Anticancer Antibodies", Science, May 30, 2013, pp. 88-91, vol. 341, No. 6141, American Association for the Advancement of Science, Washington, DC.
Zhao et al., "CD47-signal regulatory protein-α (SIRPα) interactions form a barrier for antibody-mediated tumor celldestruction", Proc Natl Acad Sci USA, Nov. 8, 2011, pp. 18342-18347, vol. 108, No. 45, PNAS, Washington,DC.
Zheng et al., "Gene expression profiling of CD34β cells identifies a molecular signature of chronic myeloid leukemiablast crisis", Leukemia, Apr. 13, 2006, pp. 1028-1034, 20, Nature Publishing Group, London, United Kingdom.

* cited by examiner

ANTI SIRP-α ANTIBODIES AND BI-SPECIFIC MACROPHAGE ENHANCING ANTIBODIES

CROSS REFERENCE

This application claims benefit and is a Continuation of application Ser. No. 15/122,560 filed Aug. 30, 2016, which is a 371 application and claims the benefit of PCT Application No. PCT/US2015/019954, filed Mar. 11, 2015, which claims benefit of U.S. Provisional Patent Application No. 61/951,226, filed Mar. 11, 2014, which applications are incorporated herein by reference in their entirety.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Unlike healthy cells, the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells, are present in an altered conformation or they are superseded by the upregulation of "eat-me" or pro-phagocytic signals. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte can cause removal of live cells bearing "eat me" signals.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

Programmed cell death (PCD) and phagocytic cell removal are common ways that an organism responds in order to remove damaged, precancerous, or infected cells. Cells that survive this host response (e.g., cancerous cells, chronically infected cells, etc.) have devised ways to evade PCD, and/or phagocytic cell removal. CD47, the "don't eat me" signal, is constitutively upregulated on a wide variety of diseased cells, cancer cells, and infected cells, allowing these cells to evade phagocytosis. Anti-CD47 agents that block the interaction between CD47 on one cell (e.g., a cancer cell, an infected cell, etc.) and SIRPα on another cell (e.g., a phagocytic cell) counteract the increase of CD47 expression and facilitate the phagocytosis of the cancer cell and/or the infected cell. Thus, anti-CD47 agents can be used to treat and/or protect against a wide variety of conditions/disorders. In fact, anti-CD47 and anti-SIRPα blocking antibodies significantly increase phagocytosis of cancer cells in vitro and in vivo. They have been shown to be effective at treating mice engrafted with a wide range of human cancers, from leukemias to solid tumors. However, in some cases an initial high dose of an anti-CD47 agent can cause a dose-dependent loss of red blood cells (RBCs) in mice and non-human primate (NHP) models by binding to CD47 on the surface of the RBCs. The severity of this anemia can preclude the use of higher doses that are required to achieve sustained serum concentrations associated with therapeutic efficacy.

The present disclosure provides anti-SIRPα antibodies that block the interaction of CD47 on one cell (e.g., a cancer cell, an infected cell, etc.) with SIRPα on another cell (e.g., a phagocytic cell), and facilitate the phagocytosis of the CD47-expressing cell. Also disclosed are antibodies that are bispecific for SIRPα and a second antigen (e.g., a tumor antigen). These bispecific macrophage enhancing (BiME) antibodies exhibit enhanced properties.

SUMMARY OF THE INVENTION

Compositions and methods are provided relating to anti-SIRPα antibodies. The antibodies of the disclosure bind to human SIRPα and can block the interaction of CD47 expressed on a target cell of interest with SIRPα expressed on a phagocytic cell. The subject antibodies find use in various therapeutic methods. In some cases, an anti-SIRPα antibody of the invention can bind SIRPα, but does not stimulate SIRPα signaling in the cell expressing the SIRPα. Embodiments of the disclosure include isolated antibodies and derivatives and fragments thereof, pharmaceutical formulations comprising one or more of the subject anti-SIRPα antibodies; and cell lines that produce these anti-SIRPα antibodies. Also provided are amino acid sequences of exemplary antibodies. Antibodies of interest include the provided anti-SIRPα antibodies, and variants thereof. The anti-SIRPα antibodies of the disclosure find particular utility as reagents for the treatment of diseases associated with CD47 in humans (e.g., cancer, chronic infection, etc.)

Various forms of the antibodies are provided herein. For example, an anti-SIRPα antibody may be a full length chimeric or humanized antibody, e.g. having a human immunoglobulin constant region of any isotype or modification, e.g. IgG1, IgG2, IgG3, IgG4, IgA, etc.; or an antibody fragment, e.g. a F(ab')$_2$ fragment, and F(ab) fragment, etc. Fragments comprising CDR regions are also of interest. Exemplary forms also include single-chain Fv species (scFv) having one heavy- and one light-chain variable domain that are covalently linked by a flexible peptide linker. Furthermore, the antibody may be labeled with a detectable label, immobilized on a solid phase and/or conjugated with a heterologous compound. The antibody may also be provided as a bispecific or multispecific antibody reactive with a second antigen, particularly including cancer antigens and/or antigens of chronic infection. The disclosure also provides compositions that include a subject anti-SIRPα antibody and an antibody that binds to a second antigen (e.g., a cancer cell marker, a marker of chronic infection, and the like).

Also provided are methods for determining the presence of SIRPα expressing cells, comprising exposing a patient sample suspected of containing SIRPα expressing cells to the anti-SIRPα antibody and determining binding of the antibody to the sample. For this use, the invention provides a kit comprising the antibody and instructions for using the antibody.

The antibodies of the disclosure are efficacious in the treatment of disease. In some embodiments of method of treatment is provided, comprising contacting an individual with an effective dose of an antibody of the invention, wherein the effective dose provides for binding the antibody of the invention to a phagocytic cell thereby increasing phagocytosis of target cells expressing CD47. Treatment may be systemic or localized, e.g. delivery by intratumoral injection, etc.

Embodiments of the disclosure include isolated antibodies and derivatives and fragments thereof that comprise at least one, usually at least 3 CDR sequences from a set, as provided herein, usually in combination with framework sequences from a human variable region. In some embodiments an antibody or derivative or fragment thereof comprises at least one light chain comprising a set of 3 light chain CDR sequences provided herein, situated in a variable region framework, which may be, without limitation, a human, canine, mouse, etc. variable region framework; and at least one heavy chain comprising the set of 3 heavy chain CDR sequence provided herein, situated in a variable region framework, which may be, without limitation, a human, canine, mouse, etc. variable region framework or other appropriate protein scaffold.

In other embodiments, the antibody comprises an amino acid sequence variant of one or more of the CDRs of the provided antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity for human SIRPα of $10^{-5}$ M or better (e.g., $10^{-6}$ M or better, $10^{-8}$ M or better, etc.) and will bind to the same epitope as an antibody having the amino acid sequence of those set forth herein.

The disclosure further provides: isolated nucleic acids encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The disclosure also provides a composition comprising one or more of the anti-SIRPα antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

(FIG. 1A-1B) Assays of KWAR23 binding to SIRPα by blocking CD47 binding to THP-1 cells (a SIRPα expressing cell line used to investigate the function and regulation of monocytes and macrophages). LH and HL monomers are engineered KWAR23 scFv monomers having a light chain with KWAR23 CDRs linked via linker to a heavy chain with KWAR23 CDRs (HL, N-terminal heavy-chain; LH, N-terminal light-chain). "Geo. MFI" is geometric mean fluorescence intensity. (FIG. 1C) KWAR23 scFv blocks CD47 binding, as assayed by measuring CD47 binding to SIRPα-displaying yeast.

(FIG. 3A) KWAR23 enhanced the efficacy of anti-CD20 for all tested IgG isotypes. (FIG. 3B) KWAR23 enhanced the efficacy of both tested isotypes of anti-EGFR (epidermal growth factor receptor). Although they both target EGFR, panitumumab (IgG2) and cetuximab (IgG1) differ in their isotype.

(FIG. 4A) Schematic of activity of exemplary subject bispecific antibodies, which activities include engaging Fc receptors on macrophages, activating ITAMs; blocking CD47-SIRP interaction, removing ITIM inhibition; and physically cross-linking macrophages to cancer cells. (FIG. 4B) Schematic of an exemplary anti-CD20 (and anti-SIRPα) BiME antibody. (FIG. 4C) Phagocytosis of Raji cells after exposure to a subject anti-CD20 (and anti-SIRPα) BiME antibody.

(FIG. 5A). Binding of the CD20 BiME to yeast expressing hSIRPα was detected by an anti-human IgG4 Fc antibody conjugated to Alexa fluor-647 and an anti-rituximab antibody conjugated to FITC. (FIG. 5B). Binding of KWAR23 to yeast expressing hSIRPα was detected by the anti-human IgG4 Fc antibody but not the anti-rituximab antibody.

(FIG. 6A-6C). Anti-SIRPα antibody (KWAR23) enhances antibody-dependent cellular phagocytosis (ADCP) of cancer-targeting antibodies by human macrophages: (FIG. 6A). KWAR23+rituximab (anti-CD20) for human lymphoma cancer cells (Raji); (FIG. 6B). KWAR23+trastuzumab (anti-Her2) for human breast cancer cells (SKBR3); (FIG. 6C). KWAR23+vorsetuzumab (anti-CD70) for human renal cell cancer (RCC10, TK10, Caki1). (FIG. 6D-6E). Anti-SIRPα antibody (KWAR23) enhances antibody-dependent cellular cytotoxicty (ADCC) of cancer-targeting antibodies by human neutrophils: (FIG. 6D). KWAR23+rituximab (anti-CD20) for human lymphoma cancer cells (Raji); (FIG. 6E). KWAR23+trastuzumab (anti-Her2) for human breast cancer cells (SKBR3).

(FIG. 7A-7C). Anti-SIRPα antibody (KWAR23) BiMEs enhance antibody-dependent cellular phagocytosis (ADCP) of cancer-targeting antibodies by human macrophages: (FIG. 7A). Anti-CD20

BiME (KWAR23+rituximab (anti-CD20)) for human lymphoma cancer cells (Raji); (FIG. 7B). Anti-Her2 BiME (KWAR23+trastuzumab (anti-Her2)) for human breast cancer cells (SKBR3); (FIG. 7C). Anti-CD70 BiME (KWAR23+vorsetuzumab (anti-CD70)) for human renal cancer (RCC10, TK10, Caki1). (FIG. 7D-7E). Anti-SIRPα antibody (KWAR23) BiMEs enhance antibody-dependent cellular cytotoxicty (ADCC) of cancer-targeting antibodies by human neutrophils: (FIG. 7D). Anti-CD20 BiME (KWAR23+rituximab (anti-CD20)) for human lymphoma cancer cells (Raji); (FIG. 7E). Anti-Her2 BiME (KWAR23+trastuzumab (anti-Her2)) for human breast cancer cells (SKBR3).

(FIG. 8A). Expression of EGFR on the surface of human colon cancer cell lines as determined by binding of cetuximab. Dotted black line represents DLD-1 cells stained with isotype control antibody. (FIG. 8B). Human macrophage phagocytosis of GFP+ colon cancer cell lines treated with the indicated therapies. Mutational status of KRAS and BRAF as previously reported. Data represent mean and standard deviation using macrophages from four independent blood donors. wt=wild-type; ns=not significant, $*p<0.05$, $p<0.01$, $**p<0.0001$ for KWAR23+cetuximab versus all other treatments or the indicated comparisons as assessed by two-way ANOVA with Sidak corrections for multiple comparisons.

DETAILED DESCRIPTION OF THE EMBODIMENTS

Figure 1A:
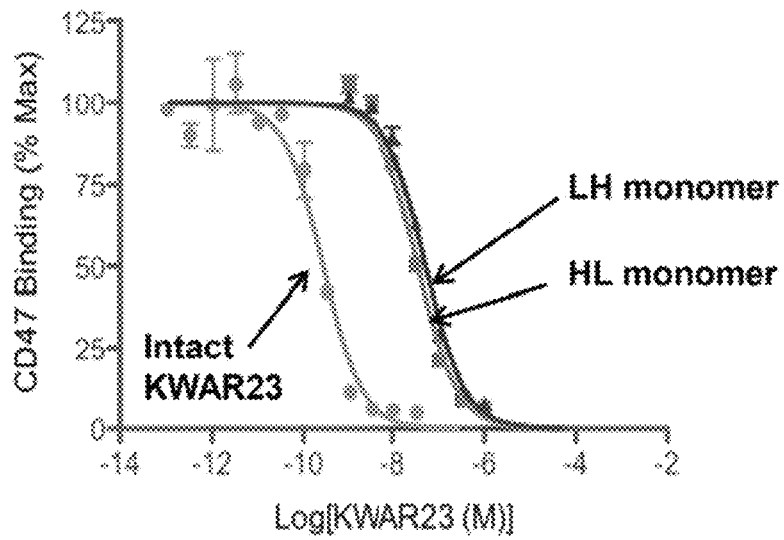
FIG. 1A-1C. KWAR23, a monoclonal CD47-blocking anti-human SIRPα antibody.
Figure 1B:
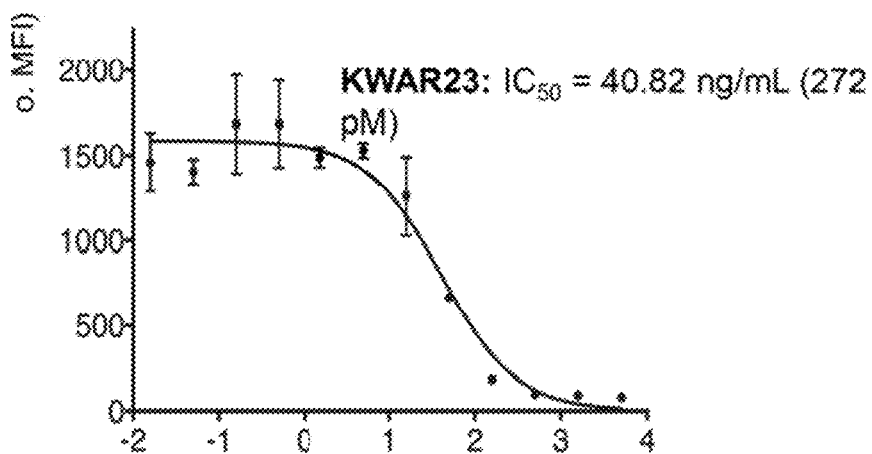
Figure 1C:
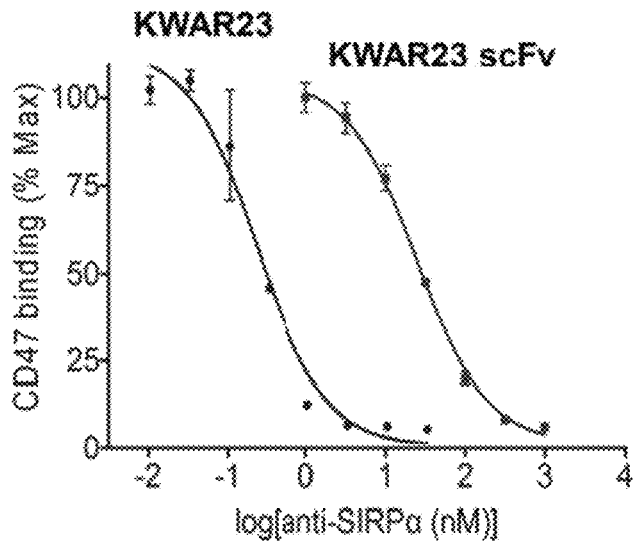
Figure 2A:
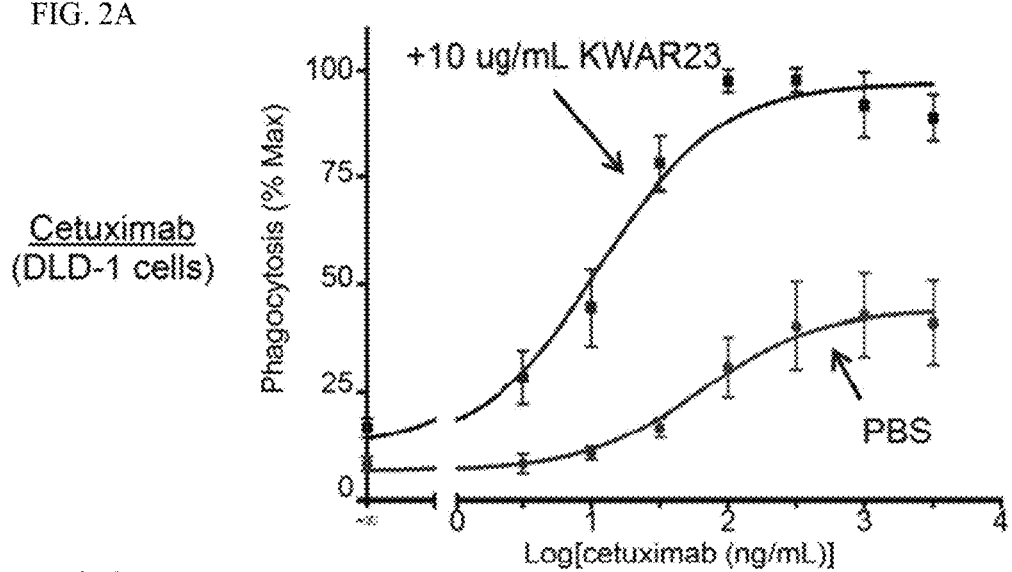
FIG. 2A-2C depicts phagocytosis of cancer cells by human macrophages in the presence of the indicated antibody (cetuximab, trastuzumab, or rituximab) plus or minus the KWAR23 antibody. Cetuximab (anti-EGFR, DLD-1 cells); Trastuzumab (anti-HER2, SKBR3 cells); and Rituximab (anti-CD20, Raji cells)
Figure 2B:
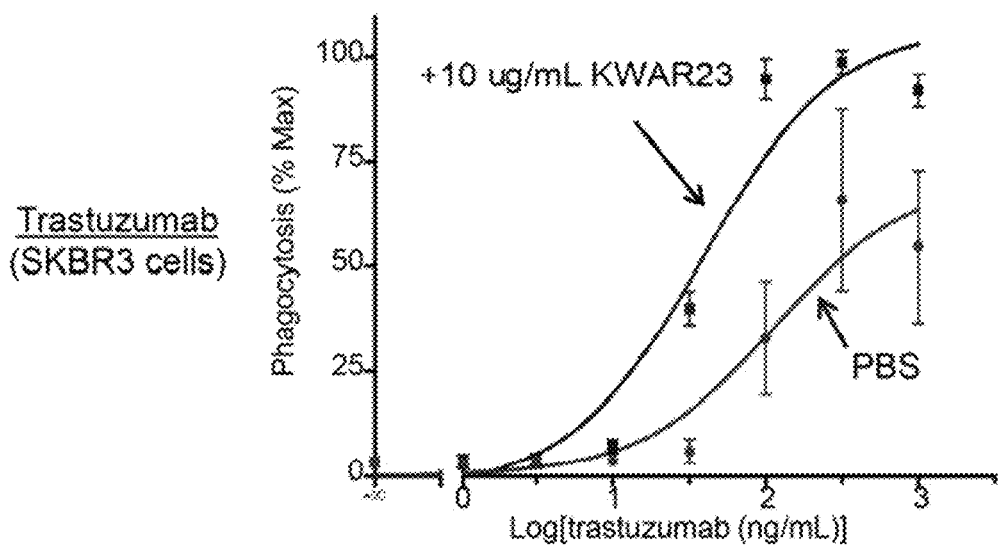
Figure 2C:
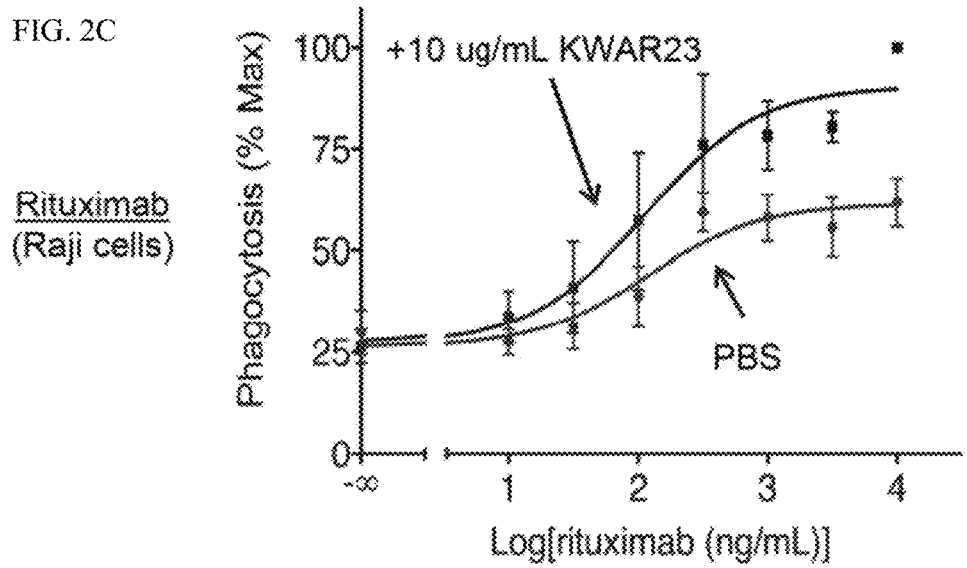
Figure 3A:
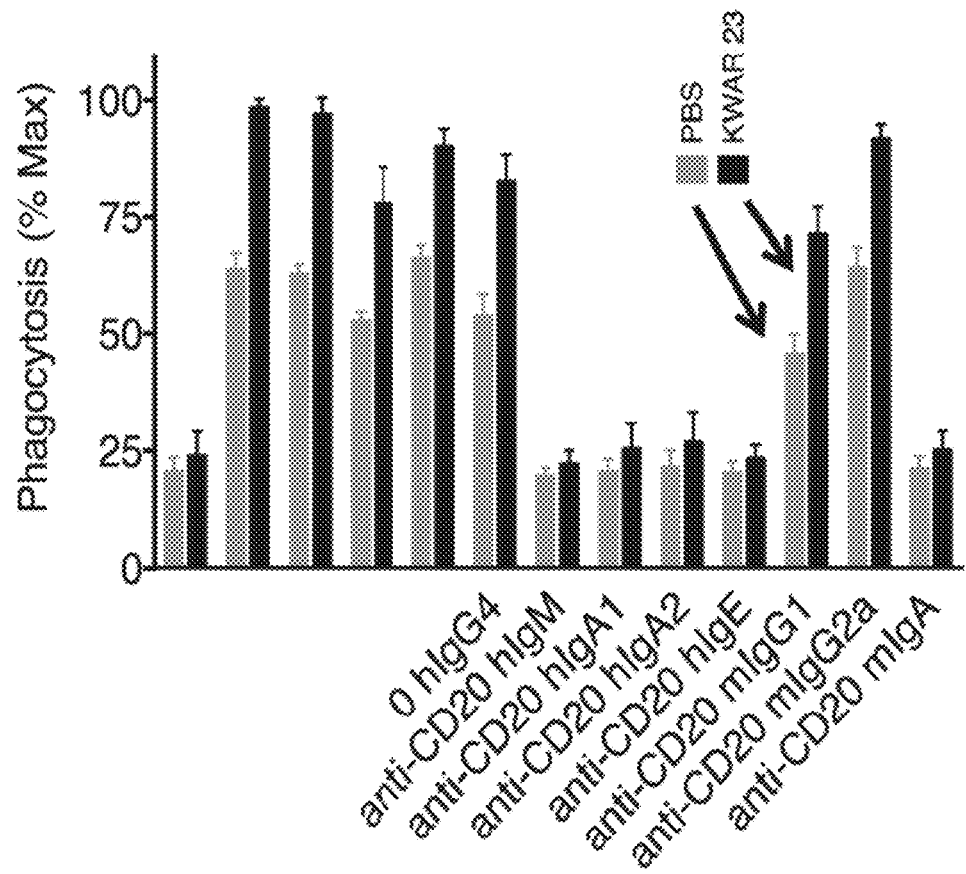
FIG. 3A-3B KWAR 23 enhances the efficacy of all human IgG isotypes.
Figure 3B:
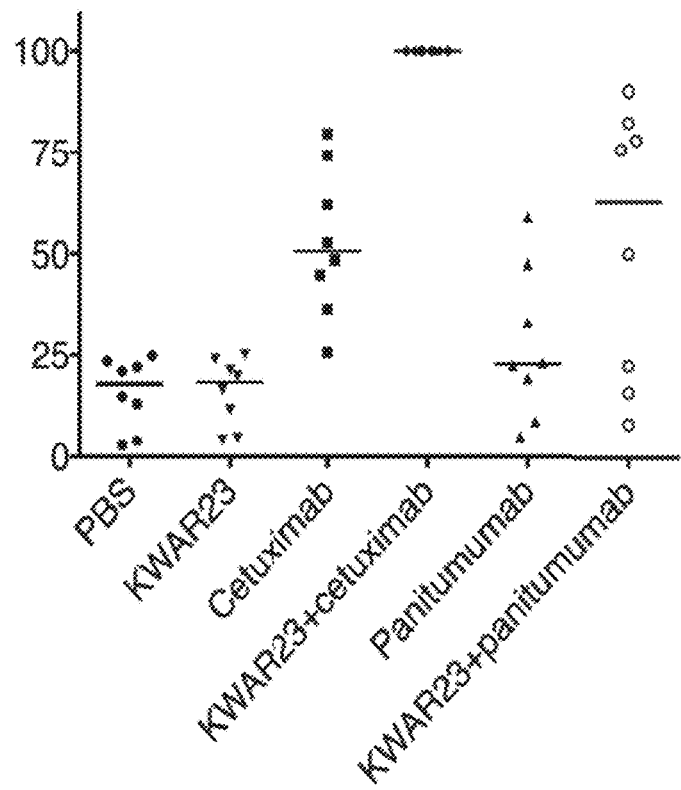

The present disclosure relates to antibodies, including without limitation humanized monoclonal antibodies, that are specific for SIRPα. Also disclosed is a nucleic acid, and amino acid sequence of such antibodies. The antibodies find use in therapeutic and diagnostic methods associated with SIRPα.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Definitions The term "target cell" can be used in different ways depending on context. Typically a "target cell" is a cell that will be phagocytosed by a phagocytic cell (e.g., a phagocyte), where the phagocytosis is enhanced as a result of administering a subject anti-SIRPα antibody. Thus, the term "target cell" can refer to a CD47-expressing cell because a subject anti-SIRPα antibody, by inhibiting the interaction between the CD47-expressing cell and the SIRPα expressing phagocytic cell, facilitates phagocytosis of the CD47-expressing cell.

However, in some cases, the target cell need not express high levels of CD47 (and in some cases need not express CD47 at all) in order for a subject multispecific antibody to induce phagocytosis of the target cell. For example, in the context of a multispecific (e.g., bispecific) antibody, the SIRPα binding region (the first binding region) of a subject multispecific (e.g., bispecific) antibody binds to SIRPα on a phagocytic cell (e.g., a macrophage), which allows the multispecific antibody to function as a tether to bring the phagocytic cell into the vicinity of a cell expressing an antigen (e.g., a marker of a cancer cell) that is recognized by (specifically bound by) a second binding region of the multispecific antibody (e.g., the second binding region of a bispecific antibody). Therefore, in the context of a multispecific antibody, a target cell can be a cell that does not express high levels of CD47 (and can also be a cell that does not express CD47). In some embodiments, a target cell is a mammalian cell, for example a human cell. A target cell can be from any individual (e.g., patient, subject, and the like) as described below.

In some cases, a target cell is an "inflicted" cell (e.g., a cell from an "inflicted" individual), where the term "inflicted" is used herein to refer to a subject with symptoms, an illness, or a disease that can be treated with a subject anti-SIRPα antibody. An "inflicted" subject can have cancer, can harbor an infection (e.g., a chronic infection), and/or can have other hyper-proliferative conditions, for example sclerosis, fibrosis, and the like, etc. "Inflicted cells" can be those cells that cause the symptoms, illness, or disease. As non-limiting examples, the inflicted cells of an inflicted patient can be CD47 expressing cancer cells, infected cells, inflammatory cells, immune cells, and the like. One indication that an illness or disease can be treated with a subject anti-SIRPα antibody is that the involved cells (i.e., the inflicted cells, e.g., the cancerous cells, the infected cells, the inflammatory cells, the immune cells, etc.) express CD47 (e.g., in some cases, an increased level of CD47 compared to normal cells of the same cell type).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

Examples of symptoms, illnesses, and/or diseases that can be treated with a subject anti-SIRPα antibody include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); and an immunological disease or disorder (e.g., an inflammatory disease)(e.g., multiple sclerosis, arthritis, and the like)(e.g., for immunosuppressive therapy). For example, any cancer, where the cancer cells express CD47 (e.g., in some cases, the cancer cells exhibit increased expression of CD47 compared to non-cancer cells), is a suitable cancer to be treated by the subject methods and compositions. A subject anti-SIRPα antibody can also be used for transplant conditioning (e.g., stem cell transplant, bone marrow transplant, etc.) (e.g., to destroy malignant cells, to provide immunosuppression to prevent the patient's body from rejecting the donor's cells/stem cells, etc.). For example, in some cases, a subject antibody combination or bispecific antibody (e.g., anti-SIRPα in combination with anti-CD117) finds use for transplant conditioning. For example, a subject antibody combination or bispecific antibody (e.g., anti-SIRPα in combination with anti-CD117) can be used for bone marrow transplant conditioning. In some cases, a subject anti-SIRPα antibody (e.g., an antibody combination) can be used for immunosuppressive therapy.

As used herein "cancer" includes any form of cancer, including but not limited to solid tumor cancers (e.g., lung, prostate, breast, bladder, colon, ovarian, pancreas, kidney, liver, glioblastoma, medulloblastoma, leiomyosarcoma, head & neck squamous cell carcinomas, melanomas, neuroendocrine; etc.) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors. Any cancer, where the cancer cells express CD47 (e.g., in some cases, the cancer cells exhibit increased expression of CD47 compared to non-cancer cells), is a suitable cancer to be treated by the subject methods and compositions (e.g., a subject anti-SIRPα antibody).

Carcinomas are malignancies that originate in the epithelial tissues. Epithelial cells cover the external surface of the body, line the internal cavities, and form the lining of glandular tissues. Examples of carcinomas include, but are not limited to: adenocarcinoma (cancer that begins in glandular (secretory) cells), e.g., cancers of the breast, pancreas, lung, prostate, and colon can be adenocarcinomas; adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, skin, etc.

Soft tissue tumors are a highly diverse group of rare tumors that are derived from connective tissue. Examples of soft tissue tumors include, but are not limited to: alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; and pleomorphic adenoma of soft tissue; and neoplasias derived from fibroblasts, myofibroblasts, histiocytes, vascular cells/endothelial cells and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to: askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; undifferentiated pleomorphic sarcoma, and the like).

A teratomas is a type of germ cell tumor that may contain several different types of tissue (e.g., can include tissues derived from any and/or all of the three germ layers: endoderm, mesoderm, and ectoderm), including for example, hair, muscle, and bone. Teratomas occur most often in the ovaries in women, the testicles in men, and the tailbone in children.

Melanoma is a form of cancer that begins in melanocytes (cells that make the pigment melanin). It may begin in a mole (skin melanoma), but can also begin in other pigmented tissues, such as in the eye or in the intestines.

Leukemias are cancers that start in blood-forming tissue, such as the bone marrow, and causes large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is effected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to: Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One kind is Hodgkin lymphoma (HL), which is marked by the presence of a type of cell called the Reed-Sternberg cell. There are currently 6 recognized types of HL. Examples of Hodgkin lymphoma include: nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to: AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to: gliomas (e.g., glioblastomas, astrocytomas, oligodendrogliomas, ependymomas, and the like), meningiomas, pituitary adenomas, vestibular schwannomas, primitive neuroectodermal tumors (medulloblastomas), etc.

As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces CD47 expression (e.g., increased CD47 expression) in at least one cell of the infected organism. For example, infectious agents include, but are not limited to bacteria, viruses, protozoans, and fungi. Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure.

The Fc region of naturally-occurring antibodies binds to elements of the complement system, and also to receptors on effector cells, including for example effector cells that mediate cytotoxicity, including specifically ADCP. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal.

In some embodiments, an antibody has constant region sequences that are characteristic of mouse, rabbit, primate, or human antibodies. In some embodiments, antibody sequence elements are humanized, primatized, chimeric, etc, as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TendAbe), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload, e.g., a detectable moiety, a therapeutic moiety, a catalytic moiety, etc., or other pendant group [e.g., polyethylene glycol, etc.

Exemplary antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins.

In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Variable region sequences of interest include the provided variable region sequences for the anti-SIRPα antibody referred to herein as "KWAR23": SEQ ID NO: 1 (variable heavy chain), and SEQ ID NO: 5 (variable light chain). The KWAR23 CDR sequences are set forth in the sequence listing, including SEQ ID NOs: 2-4 (CDRs of the variable heavy chain); and SEQ ID NOs: 6-8 (CDRs of the variable light chain). In some embodiments the CDR sequences for a particularly heavy and light chain combination as set forth in KWAR23 will be maintained in a combination, i.e. a subject antibody (e.g., a humanized antibody) will comprise both KWAR23 heavy chain CDR sequences and KWAR23 light chain CDR sequences.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, $IgA_2$. The heavy-chain constant domains that correspond to the different classes of immunoglobulins are called a, d, e, g, and m, respectively. The subunit structures and three-dimensional configurations of different classes of immunoglobulins are well known. Engineered variants of immunoglobulin subclasses, including those that increase or decrease immune effector functions, half-life, or serum-stability, are also encompassed by this terminology.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The anti-SIRPα antibodies herein include hybrid and recombinant antibodies produced by splicing a variable (including hypervariable) domain of an anti-SIRPα antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, $F(ab)_2$, and Fv), so long as they exhibit the desired biological activity.

The anti-SIRPα antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-SIRPα antibody (or fragment) fused to an "epitope tag". The epitope tag polypeptide has enough residues to provide an epitope against which an antibody can be made, yet is short enough such that it does not interfere with activity of the anti-SIRPα antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)). An additional example is a "histidine tag" or "histidine-rich affinity peptide", which is a metal ion affinity peptide that is rich in histidines (e.g., 6×His tag, HAT tag, 6×HN tag, and the like). A histidine tag can also specifically bind to an anti-His antibody.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower $K_d$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

Polypeptides

In one aspect, the present disclosure is directed to antibodies (and cell lines that produce such antibodies) that specifically bind human SIRPα (i.e., an anti-SIRPα antibody) and reduce the interaction between CD47 on one cell (e.g., a cancerous cell, an infected cell, etc.) and SIRPα on another cell (e.g., a phagocytic cell). Subject anti-SIRPα antibodies can bind SIRPα without inhibiting phagocytosis (activating or stimulating signaling through SIRPα inhibits phagocytosis). Thus, subject anti-SIRPα antibodies can bind SIRPα without activating or stimulating signaling through SIRPα (e.g., a subject anti-SIRPα antibody does not stimulate SIRPα signaling to a level that inhibits phagocytosis). In other words, subject anti-SIRPα antibodies can bind SIRPα, but block CD47-induced SIRPα signaling. Thus, suitable anti-SIRPα antibodies facilitate the preferential phagocytosis of inflicted cells (e.g., cancerous cells, infected cells, etc.) over normal cells by inhibiting CD47-induced SIRPα signaling. In some cases, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Variable regions of exemplary antibodies are provided. Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-SIRPα antibody, where a CDR may be 3, 4, 5, 6, 7, 8, 9, 10, 11, 12 or more amino acids. Alternatively, antibodies of interest include a variable region as set forth in the provided antibodies, or pairs of variable regions sequences as set forth herein.

Polypeptides of interest can include an amino acid sequence that is 80% or more, 85% or more, 90% or more, 92% or more, 95% or more, 97% or more, 98% or more, 99% or more, 99.5% or more, or 100% identical to an amino acid sequence set forth in any of SEQ ID NOs: 1-18. A subject anti-SIRPα antibody may include: (i) one or more (e.g., 2 or more, 3 or more, 4 or more, 5 or more, or 6 or more) CDR sequences (e.g., those set forth in SEQ ID NOs: 2-4 and 6-8); (ii) a complete variable region (e.g., those set forth in SEQ ID NOs: 1 and 5); (iii) single-chain variable fragments (e.g., those set forth in SEQ ID NOs: 9-10); (iv) chimeric antibody sequences (e.g., those set forth in SEQ ID NOs: 11-12); and/or (v) bispecific antibody sequences (e.g., those set forth in SEQ ID NOs: 13-18). As is known in the art, a variable region sequence may be fused to any appropriate constant region sequence.

In some embodiments a subject anti-SIRPα antibody includes one more CDRs (e.g., 2 or more, 3 or more, 4 or more, 5 or more, or 6 CDRs) that includes an amino acid sequence set forth in SEQ ID NOs: 2-4 and 6-8. A subject anti-SIRPα antibody can include a CDR sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 2-4 and 6-8.

In some cases, a subject anti-SIRPα antibody includes one or more CDRs (e.g., 2 or more, 3 or more, 4 or more, 5 or more, 6, or 6 or more) having an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 2-4 and 6-8. In some cases, a subject anti-SIRPα antibody includes two or more CDRs (e.g., 3 or more, 4 or more, 5 or more, 6, or 6 or more) that have an amino acid sequence that differs by up to 6 amino acids (e.g., up to 5 amino acids, up to 4 amino acids, up to 3 amino acids, up to 2 amino acids, or up to 1 amino acid) as compared to a CDR amino acid sequence set forth in any of SEQ ID NOs: 2-4 and 6-8.

In some embodiments, a subject anti-SIRPα antibody includes an amino acid sequence that is 80% or more, 85% or more, 90% or more, 92% or more, 95% or more, 97% or more, 98% or more, 99% or more, 99.5% or more, or 100% identical to a CDR amino acid sequence set forth in any of SEQ ID NOs: 2-4 and 6-8. In some cases, a subject anti-SIRPα antibody includes a heavy chain having one or more (e.g., two or more, three or more, or 3) of the amino acid sequences set forth in SEQ ID NOs: 2-4. In some cases, a subject anti-SIRPα antibody includes a heavy chain having all 3 of the amino acid sequences set forth in SEQ ID NOs: 2-4. In some cases, a subject anti-SIRPα antibody includes a light chain having one or more (e.g., two or more, three or more, or 3) of the amino acid sequences set forth in SEQ ID NOs: 6-8. In some cases, a subject anti-SIRPα antibody includes a light chain having all 3 of the amino acid sequences set forth in SEQ ID NOs: 6-8.

In some cases, a subject anti-SIRPα antibody includes a light chain having all 3 of the amino acid sequences set forth in SEQ ID NOs: 6-8, and a heavy chain having all 3 of the amino acid sequences set forth in SEQ ID NOs: 2-4.

In some cases, a subject anti-SIRPα antibody includes a heavy chain having three CDRs, where CDR-H1 has the amino acid sequence set forth in SEQ ID NO: 2, CDR-H2 has the amino acid sequence set forth in SEQ ID NO: 3, and CDR-H3 has the amino acid sequence set forth in SEQ ID NO: 4. In some cases, a subject anti-SIRPα antibody includes a light chain having three CDRs, where CDR-L1 has the amino acid sequence set forth in SEQ ID NO: 6, CDR-L2 has the amino acid sequence set forth in SEQ ID NO: 7, and CDR-L3 has the amino acid sequence set forth in SEQ ID NO: 8. In some cases, a subject anti-SIRPα antibody includes: (i) a heavy chain having three CDRs, where CDR-H1 has the amino acid sequence set forth in SEQ ID NO: 2, CDR-H2 has the amino acid sequence set forth in SEQ ID NO: 3, and CDR-H3 has the amino acid sequence set forth in SEQ ID NO: 4; and (ii) a light chain having three CDRs, where CDR-L1 has the amino acid sequence set forth in SEQ ID NO: 6, CDR-L2 has the amino acid sequence set forth in SEQ ID NO: 7, and CDR-L3 has the amino acid sequence set forth in SEQ ID NO: 8.

In some cases, a subject anti-SIRPα antibody includes a heavy chain having an amino acid sequence as set forth in any one of SEQ ID NOs: 9-10, which are examples of single-chain variable fragments. In some cases, a subject anti-SIRPα antibody includes a heavy chain having an amino acid sequence as set forth in any one of SEQ ID NOs: 1, 11, 13, 15, and 17. In some cases, a subject anti-SIRPα antibody includes a light chain having an amino acid sequence as set forth in any one of SEQ ID NOs: 5, 12, 14, 16, and 18. In some cases, a subject anti-SIRPα antibody includes a heavy chain having an amino acid sequence as set forth in any one of SEQ ID NOs: 1, 11, 13, 15, and 17; and a light chain having an amino acid sequence as set forth in any one of SEQ ID NOs: 5, 12, 14, 16, and 18.

In some cases, a subject anti-SIRPα antibody includes a heavy chain having the amino acid sequence of SEQ ID NO: 1, and a light chain having the amino acid sequence of SEQ ID NO: 5. In some cases, a subject anti-SIRPα antibody includes a heavy chain having the amino acid sequence of SEQ ID NO: 11, and a light chain having the amino acid sequence of SEQ ID NO: 12. In some cases, a subject anti-SIRPα antibody includes a heavy chain having the amino acid sequence of SEQ ID NO: 13, and a light chain having the amino acid sequence of SEQ ID NO: 14. In some cases, a subject anti-SIRPα antibody includes a heavy chain having the amino acid sequence of SEQ ID NO: 15, and a light chain having the amino acid sequence of SEQ ID NO: 16. In some cases, a subject anti-SIRPα antibody includes a heavy chain having the amino acid sequence of SEQ ID NO: 17, and a light chain having the amino acid sequence of SEQ ID NO: 18.

In some embodiments, a subject antibody is a bispecific antibody. The terms "multispecific" or "bispecific" antibodies (also known as bifunctional antibodies or multifunctional antibodies) refer to antibodies that recognize two or more different antigens by virtue of possessing at least one region (e.g., derived from a variable region of a first antibody) that is specific for a first antigen, and at least a second region (e.g., derived from a variable region of a second antibody) that is specific for a second antigen. A bispecific antibody specifically binds to two target antigens and is thus one type of multispecific antibody. Multispecific antibodies can be produced by recombinant DNA methods or include, but are not limited to, antibodies produced chemically by any convenient method. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

Figure 4A:
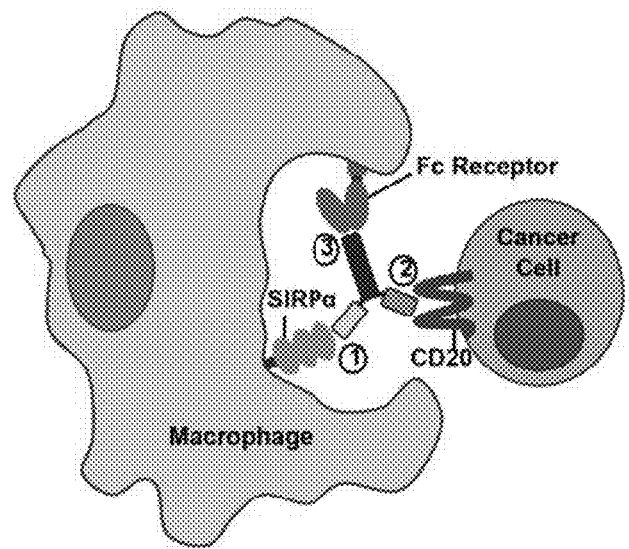
FIG. 4A-4C. Bispecific Macrophage Enhancing (BiME) antibodies.
Figure 4B:
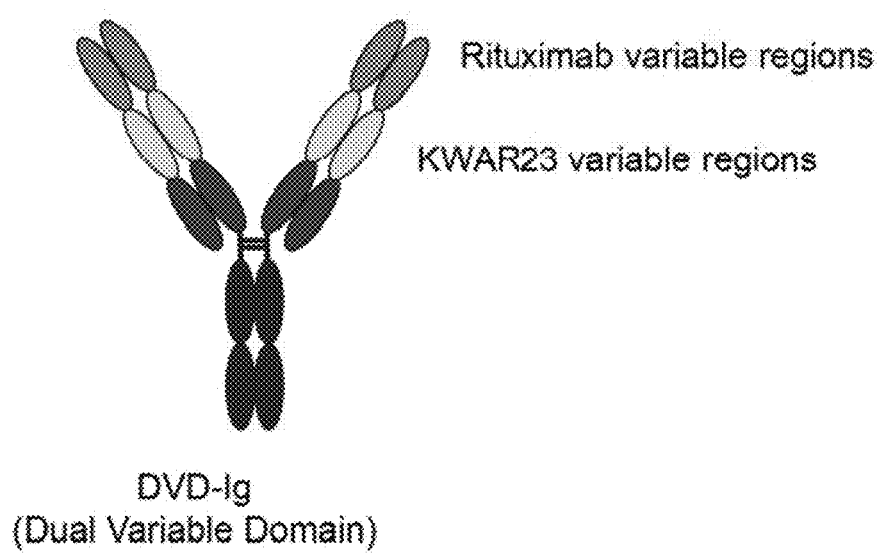
Figure 4C:
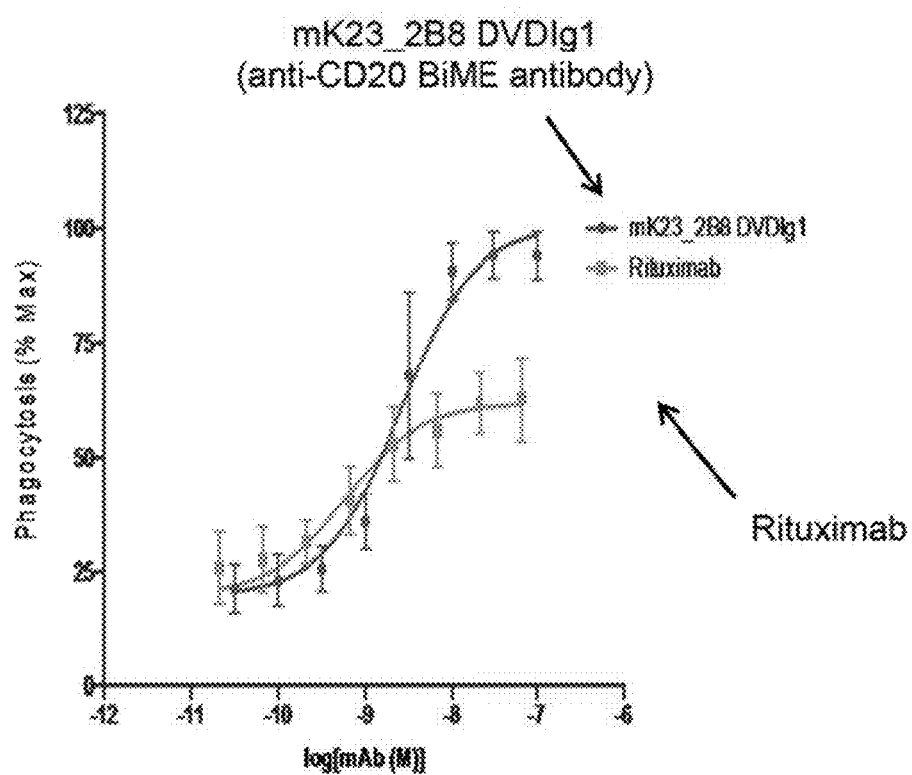
Figure 5A:
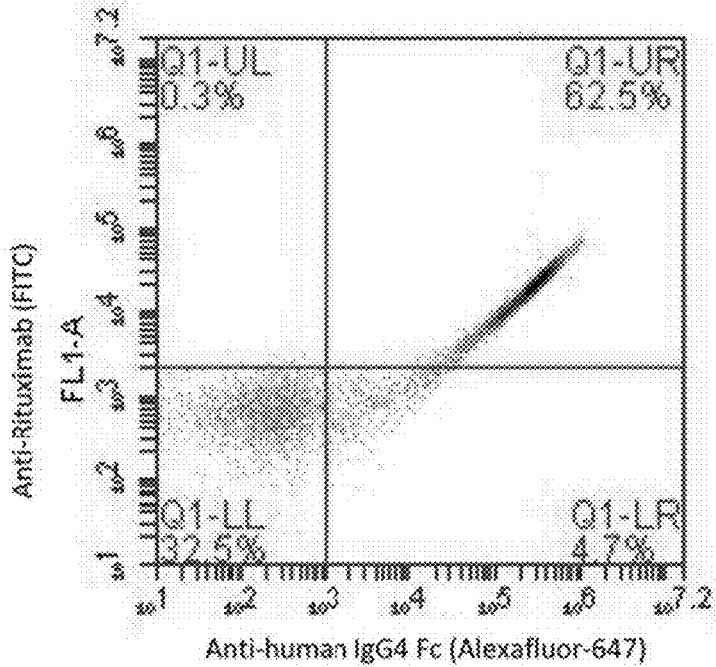
FIG. 5A-5B. Demonstration of the bispecificity of the CD20 BiME by FACS.
Figure 5B:
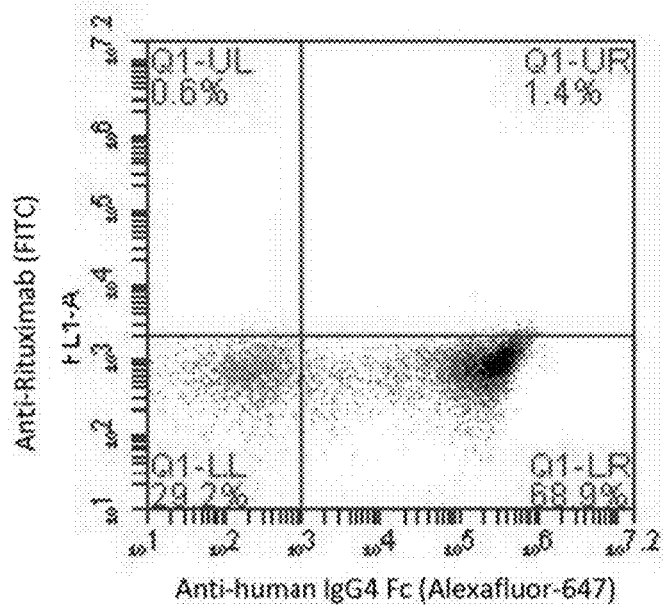
Figure 6A:
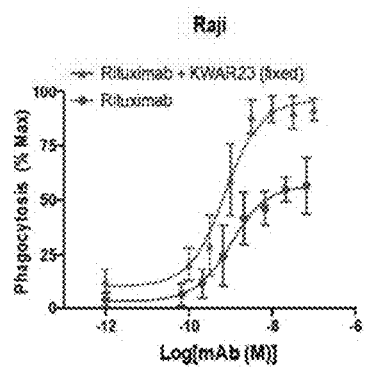
FIG. 6A-6E. Anti-SIRPα antibody (KWAR23) enhances ADCP and ADCC of cancer-targeting antibodies.
Figure 6B:
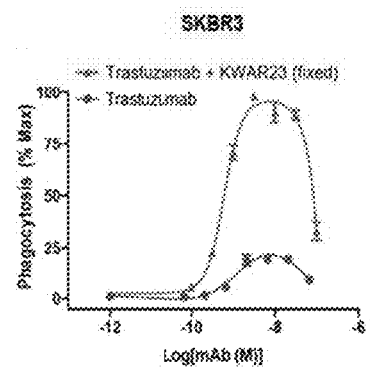
Figure 6C:
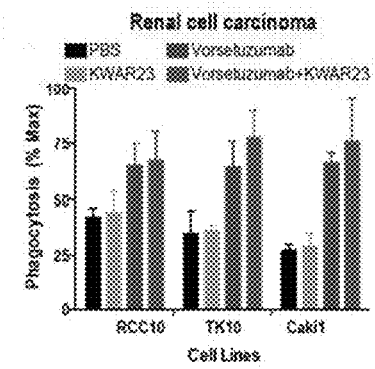
Figure 6D:
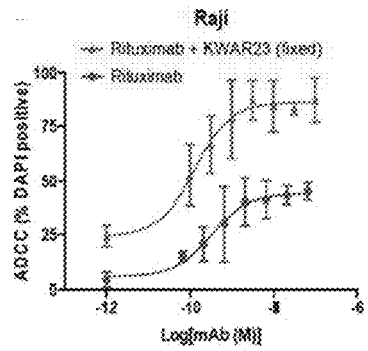
Figure 6E:
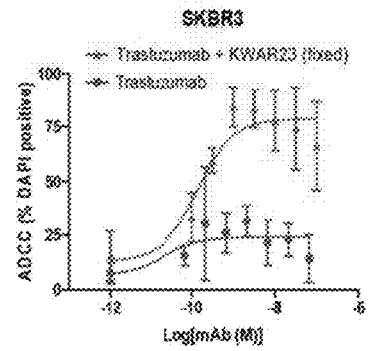
Figure 7A:
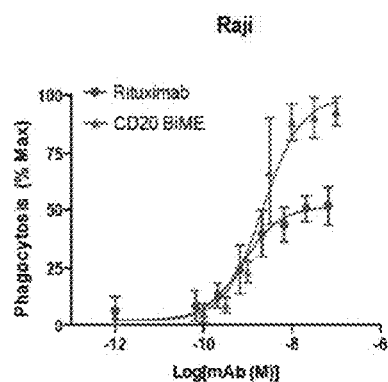
FIG. 7A-7E. Bispecific macrophages enhancing antibodies (BiMEs) enhance ADCP and ADCC compared to the parental cancer-targeting antibodies.
Figure 7B:
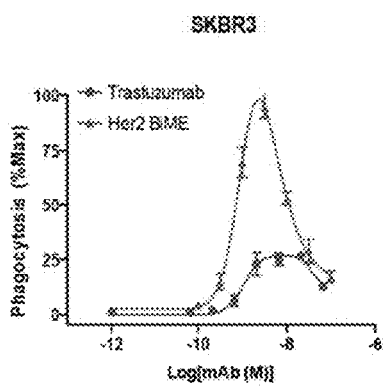
Figure 7C:
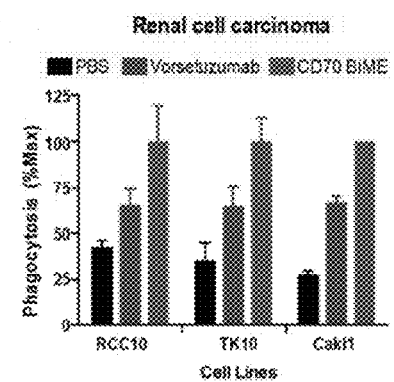
Figure 7D:
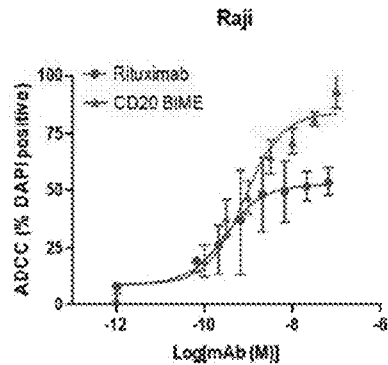
Figure 7E:
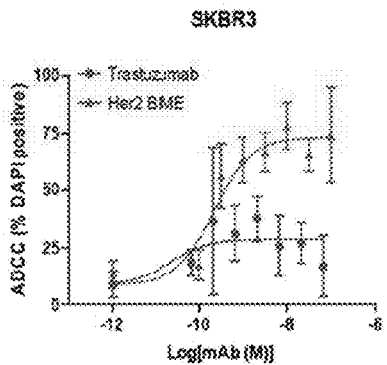

In some cases, the SIRPα binding region (the first binding region) of a subject multispecific (e.g., bispecific) antibody binds to SIRPα on a macrophage and the multispecific antibody thereby functions as a tether to bring the SIRPα-expressing phagocytic cell into the vacinity of a cell that expresses the antigen that is recognized by (specifically bound by) a second binding region of the multispecific antibody (e.g., the second binding region of a bispecific antibody). Thus, in some cases, the target cell need not express high levels of CD47 (and in some cases need not express CD47 at all) in order for a subject multispecific antibody to induce phagocytosis of the target cell. For example, an Fc region of a multispecific antibody can be recognized by the phagocytic cell (see FIG. 4). Thus, in some cases, a subject multispecific (e.g, bispecific) antibody includes a pro-phagocytic antibody Fc chain.

Subject bispecific antibodies are directed against SIRPα and a second antigen. Subject bispecific antibodies will allow for the phagocytosis of cellular populations expressing the second antigen (see FIG. 4). Exemplary bispecific antibodies include those targeting a combination of SIRPα and a cancer cell marker, such as, CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), etc. As such, in some cases, a subject antibody is a bispecific or multispecific antibody that specifically binds to SIRPα and at least a second antigen. In some such cases, the second antigen is selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3).

In some cases, an exemplary bispecific antibody includes a sequence (e.g., CDRs) disclosed herein that provides specific binding to SIRPα as well as sequences (e.g., CDRs) from antibodies that bind a cancer cell marker. Examples of antibodies with CDRs that provide specific binding to a cancer cell marker include, but are not limited to: CETUX-IMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), BRENTUXIMAB (binds CD30), and the like.

Methods to generate bispecific antibodies are described in the literature, for example, in U.S. Pat. Nos. 5,989,830, 5,798,229, which are incorporated herein by reference. Higher order specificities, e.g. trispecific antibodies, are described by Holliger and Hudson (2005) Nature Biotechnology 23:1126-1136.

Traditional production of full-length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. An alternative method links two different single chain variable regions to heat stable antigen (HSA). Using HSA as linker increases serum half life, and has the benefit of low immunogenicity.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_{H1}$-$V_H$-$C_H$1) which form a pair of antigen binding regions. Linear antibodies can be bispecific or monospecific.

Dual variable domain (DVD) bispecific antibodies and methods to generate them have also been described (e.g., see Wu et al., Nat Biotechnol. 2007 November; 25(11):1290-7, Gu et al., Methods Enzymol. 2012; 502:25-41, and U.S. patent applications, 20130195871, 20130171059, 20130004416, 20120263722, 20120258108, 20120189541, 20120087858, 20120034160, 20120014957, 20110318349, 20110263827, 20110212094, 20110091463, 20110091372, 20110044980, 20110008766, 20100260668, 20100233079, 20100076178, 20100047239, 20090311253, 20090304693, 20090215992, and 20070071675; all of which are hereby incorporated by reference in their entirety). In this format, the target-binding variable domains of two polypeptides (e.g., two monoclonal antibodies) can be combined via linkers to create a tetravalent, multi-targeting (e.g., dual-targeting) single agent (bispecific and/or multispecific antibody). The produced agent can be a dual-specific, tetravalent immunoglobulin G (IgG)-like molecule, termed dual-variable-domain immunoglobulin (DVD-Ig), that can be engineered from any two antibodies (e.g., monoclonal antibodies) while preserving activities of the parental antibodies. This type of molecule can be efficiently produced from mammalian cells and exhibits good physicochemical and pharmacokinetic properties.

Within the context of the present disclosure, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies of the present disclosure may also be described or specified in terms of their binding affinities, including those characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). For bispecific and/or multispecific antibodies, which have more than one specificity (i.e., more than 1 binding constant), each antigen-specific region can have a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less).

In addition to Fabs, smaller antibody fragments and epitope-binding peptides having binding specificity for at least one epitope of SIRPα are also contemplated by the present disclosure and can also be used in the subject methods. For example, single chain antibodies can be constructed according to the method of U.S. Pat. No. 4,946,778 to Ladner et al, which is incorporated herein by reference in its entirety. Single chain antibodies can include the variable regions of the light and heavy chains joined by a flexible linker moiety. Exemplary suitable single chain antibodies can include an amino acid sequence set forth herein (e.g., SEQ ID NOs: 2-4, 6-8, and/or 9-10) (SEQ ID NOs: 2-4 and 6-8 are CDRs) (SEQ ID NO: 9 is KWAR23 scFv Heavy-Light) (SEQ ID NO: 10 is KWAR23 scFv Light-Heavy).

Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form.

Nucleic Acids

The disclosure also provides isolated nucleic acids encoding subject anti-SIRPα antibodies (e.g., including any of the polypeptides discussed above), vectors and host cells comprising the nucleic acid, and recombinant techniques for the production of the antibody. Nucleic acids of interest may encode an amino acid sequence that is 80% or more, 85% or more, 90% or more, 92% or more, 95% or more, 97% or more, 98% or more, 99% or more, 99.5% or more, or 100% identical to an amino acid sequence set forth in any of SEQ ID NOs: 1-18. Subject nucleic acids may include sequences that encode (i) one or more (e.g., 2 or more, 3 or more, 4 or more, 5 or more, or 6 or more) CDR sequences (e.g., those set forth in SEQ ID NOs: 2-4 and 6-8); (ii) a complete variable region (e.g., those set forth in SEQ ID NOs: 1 and 5); (iii) single-chain variable fragments (e.g., those set forth in SEQ ID NOs: 9-10); (iv) chimeric antibody sequences (e.g., those set forth in SEQ ID NOs: 11-12); and/or (v) bispecific antibody sequences (e.g., those set forth in SEQ ID NOs: 13-18). As is known in the art, a variable region sequence may be fused to any appropriate constant region sequence.

For recombinant production of the antibody, the nucleic acid encoding can be inserted into a replicable vector for further cloning (amplification of the DNA) or for expression. DNA encoding a subject antibody can be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

A subject anti-SIRPα antibody of this disclosure may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Examples of suitable host cells for cloning or expressing subject nucleic acids include, but are not necessary limited to prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for anti-SIRPα antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human g1, g2, or g4 heavy chains (Lindmark et al., J. Immunol. Meth. 62:1-13 (1983)). Protein G is usually recommended for human g3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The subject anti-SIRPα antibodies provided herein can be used in the modulation of phagocytosis (e.g. inducing phagocytosis). For example, the subject anti-SIRPα antibodies provided herein can be used, in any method where the interaction between CD47 on one cell and SIRPα on another is to be blocked. Exemplary methods for using a subject anti-SIRPα antibody include, but are not limited to those methods described in U.S. patent applications: 20130142786, 20120282174, 20110076683, 20120225073, 20110076683, 20110015090, 20110014119, 20100239579, 20090191202, 20070238127, 20070111238, and 20040018531; which are hereby specifically incorporated by reference in their entirety. For example, antibody compositions may be administered to induce phagocytosis of cancer cells, inflammatory cells, and/or chronically infected cells that express CD47.

A subject anti-SIRPα antibody provided herein may administered, alone or in combination with another antibody (e.g., in the form of a bispecific antibody) to a subject to treat symptoms, illnesses, and/or diseases. Examples of symptoms, illnesses, and/or diseases that can be treated with a subject anti-SIRPα antibody include, but are not limited to cancer (any form of cancer, including but not limited to: carcinomas, soft tissue tumors, sarcomas, teratomas, melanomas, leukemias, lymphomas, brain cancers, solid tumors, mesothelioma (MSTO), etc.); infection (e.g., chronic infection); and immunological diseases or disorders (e.g., an inflammatory disease)(e.g., multiple sclerosis, arthritis, and the like)(e.g., for immunosuppressive therapy). A subject anti-SIRPα antibody can also be used for transplant conditioning (e.g., stem cell transplant, bone marrow transplant, etc.) (e.g., to destroy malignant cells, to provide immunosuppression to prevent the patient's body from rejecting the donor's cells/stem cells, etc.)

As used herein "cancer" includes any form of cancer as described herein. Any cancer where the cancer cells express CD47 (e.g., in some cases, the cancer cells exhibit increased expression of CD47 compared to non-cancer cells), is a suitable cancer to be treated by the subject methods and compositions.

In some embodiments, subject anti-SIRPα antibodies can inhibit activation of an immune cell, and thus may inhibit cytokine and/or chemokine production of immune cells, particularly immune cells that express CD47 on the cell surface. The presence of an immune complex (i.e., an antigen-antibody complex) interacting with an immune cell activates the immune cell and induces cytokine production by the immune cell, which can be inhibited by a subject anti-SIRPα antibody. Immune complexes can damage tissue by triggering Fc-receptor mediated inflammation, a process implicated in several human immunological diseases, for example, systemic lupus erythematosus, rheumatoid arthritis, and Sjoergen's syndrome. Thus, the subject anti-SIRPα antibodies described herein may be useful for altering immunoresponsiveness of an immune cell and thereby may be useful for treating or preventing an immunological disease or disorder.

A subject anti-SIRPα antibody can be useful for treating or preventing, inhibiting, slowing the progression of, or reducing the symptoms associated with, an immunological disease or disorder. An immunological disorder includes an inflammatory disease or disorder and an autoimmune disease or disorder. While inflammation or an inflammatory response is a host's normal and protective response to an injury, inflammation can cause undesired damage. For example, atherosclerosis is, at least in part, a pathological response to arterial injury and the consequent inflammatory cascade. A cardiovascular disease or disorder that may be treated, which may include a disease or disorder that is also considered an immunological disease/disorder, includes for example, atherosclerosis, endocarditis, hypertension, or peripheral ischemic disease. A metabolic disease or disorder includes diabetes, obesity, and diseases and disorders associated with abnormal or altered mitochondrial function.

An immunological disease or disorder may be an autoimmune disease or an inflammatory disease. In certain embodiments, the immunological disease or disorder is multiple sclerosis, rheumatoid arthritis, a spondyloarthropathy, systemic lupus erythematosus, graft versus host disease, an antibody-mediated inflammatory or autoimmune disease or disorder, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, or inflammatory autoimmune myositis. A spondyloarthropathy includes, for example, ankylosing spondylitis, reactive arthritis, enteropathic arthritis associated with inflammatory bowel disease, psoriatic arthritis, isolated acute anterior uveitis, undifferentiated spondyloarthropathy, Behcet's syndrome, and juvenile idiopathic arthritis. The anti-SIRPα antibodies described herein may also be useful for treating a cardiovascular disease or disorder, such as atherosclerosis, endocarditis, hypertension, or peripheral ischemic disease. In certain embodiments, the inflammatory disease is multiple sclerosis or arthritis (e.g., rheumatoid arthritis). For example, in some cases, a subject antibody combination or bispecific antibody (e.g., anti-SIRPα in combination with anti-CD19, CD20, CD22, CD 52, and the like) finds use for treating inflammatory disease. For example, a subject antibody combination or bispecific antibody (e.g., anti-SIRPα in combination with anti-CD19, CD20, CD22, CD 52, and the like) can be used for therapeutic B cell depletion.

In some embodiments, a subject anti-SIRPα antibody can be used to alter (enhance or suppress in a statistically significant or biologically significant manner) the immunoresponsiveness of an immune cell. A subject anti-SIRPα antibody described herein may alter or affect the immunoresponsiveness of an immune cell by effecting a biological function or action, including any one or more (or at least one of) the following: inhibiting maturation of dendritic cells; impairing development of naive T cells into Th1 effector cells; suppressing cytokine release by dendritic cells; altering cell migration; inhibiting production of at least one cytokine, for example, at least one of TNF-.alpha., IL-12, IL-23, IFN-.gamma., GM-CSF, and IL-6; inhibiting immune complex-induced production of at least one cytokine by an immune cell, such, for example, a dendritic cell; inhibiting activation of an immune cell that expresses a CCD47 ligand, for example SIRP-alpha, inhibiting production of a chemokine by an immune cell; inhibiting Fc-mediated cytokine production; and suppressing a proinflammatory response.

In general, an immune response includes (1) a humoral response, in which antibodies specific for antigens are produced by differentiated B lymphocytes known as plasma cells, and (2) a cell mediated response, in which various types of T lymphocytes act to eliminate antigens by a number of mechanisms. For example, helper T cells that are capable of recognizing specific antigens may respond by releasing soluble mediators such as cytokines to recruit additional cells of the immune system to participate in an immune response. Also, cytotoxic T cells that are also capable of specific antigen recognition may respond by binding to and destroying or damaging an antigen-bearing cell or particle.

An immune response in a host or subject may be determined by any number of well-known immunological methods. Such assays include, but are not limited to, in vivo or in vitro determination of soluble antibodies, soluble mediators such as cytokines (e.g., IFN-.gamma., IL-2, IL-4, IL-10, IL-12, IL-6, IL-23, TNF-.alpha., and TGF-.beta.), lymphokines, chemokines, hormones, growth factors, and the like, as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cell maturation, such as maturation of dendritic cells in response to a stimulus; alteration in relationship between a Th1 response and a Th2 response; cellular differentiation by cells of the immune system, including altered surface antigen expression profiles or the onset of apoptosis (programmed cell death). Procedures for performing these and similar assays are may be found, for example, in Lefkovits (Immunology Methods Manual: The Comprehensive Sourcebook of Techniques, 1998). See also Current Protocols in Immunology; Weir, Handbook of Experimental Immunology, Blackwell Scientific, Boston, Mass. (1986); Mishell and Shigii (eds.) Selected Methods in Cellular Immunology, Freeman Publishing, San Francisco, Calif. (1979); Green and Reed, Science 281:1309 (1998) and references cited therein).

Levels of cytokines may be determined according to any convenient method, including ELISA, ELISPOT, mass spectrometry, and flow cytometry (to measure intracellular cytokines). Immune cell proliferation and clonal expansion resulting from an antigen-specific elicitation or stimulation of an immune response may be determined by isolating lymphocytes, such as spleen cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of a subject anti-SIRPα antibody described herein on the balance between a Th1 immune response and a Th2 immune response may be examined, for example, by determining levels of Th1 cytokines, such as IFN-.gamma., IL-12, IL-2, and TNF-.beta., and Type 2 cytokines, such as IL-4, IL-5, IL-9, IL-10, and IL-13.

For example, in some cases, a subject antibody combination or bispecific antibody (e.g., anti-SIRPα in combination with anti-CD19, CD20, CD22, CD 52, and the like) finds use for treating an inflammatory disease. For example, a subject antibody combination or bispecific antibody (e.g., anti-SIRPα in combination with anti-CD19, CD20, CD22, CD 52, and the like) can be used for therapeutic B cell depletion.

A subject anti-SIRPα antibody provided herein may be used in a method of vaccination against human pathogens and/or or human cancer. For example, a patient's own SIRPα expressing phagocytic cells (e.g., macrophages, e.g., autologous macrophages) could be combined (e.g., ex vivo/in vitro) with inflicted cells (e.g., cancer cells, cells with an intracellular infection, etc.), and treated with a subject anti-SIRPα antibody to induce uptake (e.g, phagocytosis). The phagocytic cells could be transplanted back into the patient to present antigens (e.g., antigens from the cancer cells, antigens from the pathogen, and the like) to the host immune system, thereby generating an adaptive immune response.

The subject anti-SIRPα antibodies provided herein may be used in vitro in immunoassays in which they can be utilized in liquid phase or bound to a solid phase carrier. In addition, the anti-SIRPα antibodies in these immunoassays can be detectably labeled in various ways. Examples of types of immunoassays which can utilize anti-SIRPα antibodies of the disclosure are flow cytometry, e.g. FACS, MACS, immunohistochemistry, competitive and non-competitive immunoassays in either a direct or indirect format; and the like. Detection of the antigens using the antibodies of the disclosure can be performed utilizing immunoassays which are run in either the forward, reverse, or simultaneous modes, including immunohistochemical assays on physiological samples. Those of skill in the art will know, or can readily discern, other immunoassay formats without undue experimentation.

The anti-SIRPα antibodies of the disclosure can be bound to many different carriers and used to detect the presence of SIRPα expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding anti-SIRPα antibodies, or will be able to ascertain such, using routine experimentation.

There are many different labels and methods of labeling known to those of ordinary skill in the art (e.g., to generate a subject anti-SIRPα antibody that is detectably labeled), which find use as tracers in therapeutic methods, for use in diagnostic and/or prognostic methods, and the like. A label may be covalently or non-covalently attached to an antibody of the disclosure or a fragment thereof, including fragments consisting or comprising of CDR sequences. Examples of the types of labels which can be used in the present disclosure include enzymes, radioisotopes, fluorescent compounds, colloidal metals, chemiluminescent compounds, and bio-luminescent compounds. Those of ordinary skill in the art will know of other suitable labels for binding to the anti-SIRPα antibodies of the disclosure, or will be able to ascertain such, using routine experimentation. Furthermore, the binding of these labels to the anti-SIRPα antibodies of the disclosure can be done using standard techniques common to those of ordinary skill in the art.

In some embodiments, a subject anti-SIRPα antibody (e.g., a labeled anti-SIRPα antibody) can be used for imaging (e.g., for imaging cancer, for imaging inflammation, and the like). For example, a subject anti-SIRPα antibody can be used in a method of detecting SIRPα expressing cells in an individual. Because a subject anti-SIRPα antibody can be used to target specific cells (e.g., SIRPα expressing phagocytic cells, e.g., macrophages), the subject anti-SIRPα antibodies can be used to detect the presence of such cells (e.g., SIRPα expressing phagocytic cells) in body regions of interest (e.g., in a tumor, in an inflamed region, in an infected region, etc.). In some cases, the detection of SIRPα expressing phagocytic cells using a subject anti-SIRPα antibody (e.g., by using a subject anti-SIRPα antibody for imaging) can be used for diagnostic and/or prognostic purposes. For example, a subject anti-SIRPα antibody can be used to detect tumor-associated macrophages, which correlate with poor prognosis in many types of cancer. As another example, a subject anti-SIRPα antibody can be used to detect inflammation- and/or infection-associated macrophages. In some cases, a subject anti-SIRPα antibody is labeled with a radioisotope (i.e., the antibody is radiolabeled) and used in a method of imaging cancer, inflammation, and/or infection, for example, via positron emission tomography (PET), single-photon emission computed tomography (SPECT), and the like.

In some embodiments the antibody or a fragment thereof is attached to a nanoparticle, e.g. for use in imaging. Useful nanoparticles are those known in the art, for example including without limitation, Raman-silica-gold-nanoparticle (R—Si—Au—NP). The R—Si—Au-NPs consist of a Raman organic molecule, with a narrow-band spectral signature, adsorbed onto a gold core. Because the Raman organic molecule can be changed, each nanoparticles can carry its own signature, thereby allowing multiple nanoparticles to be independently detected simultaneously by multiplexing. The entire nanoparticle is encapsulated in a silica shell to hold the Raman organic molecule on the gold nanocore. Optional polyethylene glycol (PEG)-ylation of R—Si—Au-NPs increases their bioavailability and provides functional "handles" for attaching targeting moieties (see Thakor et al (2011) Sci Transl Med. 3(79):79ra33; Jokerst et al. (2011) Small. 7(5):625-33; Gao et al. (2011) Biomaterials. 32(8):2141-8; each herein specifically incorporated by reference).

For purposes of the disclosure, SIRPα may be detected by the anti-SIRPα antibodies of the disclosure when present in biological fluids and on tissues, in vivo or in vitro. Any sample containing a detectable amount of SIRPα can be used. A sample can be a liquid such as urine, saliva, cerebrospinal fluid, blood, serum and the like, or a solid or semi-solid such as tissues, feces, biopsies, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

In some embodiments, a subject anti-SIRPα antibody (including, for example, a bispecific macrophage engaging antibody) is used in combination with another antibody to treat an individual. In one embodiment, a subject anti-SIRPα antibody can be combined (co-administered) with monoclonal antibodies directed against one or more cancer markers (e.g., CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), and the like). In some cases, the combination compositions can be synergistic in enhancing phagocytosis of target cells as compared to the use of single antibodies. As proof of principle, CD47-directed agents (e.g., anti-CD47 antibodies) exhibit profound anti-tumor synergy with monoclonal antibodies (mAbs) against tumor-specific antigens, such as rituximab (anti-CD20) for B-cell lymphoma and trastuzumab (anti-HER2) for HER2+ breast cancer. The Fc fragments of these mAbs activate Fc receptors (FcRs) on macrophages to drive a phosphorylation cascade propagated by the receptors' ITAMs (Immunoreceptor Tyrosine-based Activation Motifs). As SIRPα signals through counter-opposing ITIMs (Immunoreceptor Tyrosine-based Inhibitory Motifs), blocking SIRPα tips the balance in favor of ITAM signaling, thereby potentiating phagocytosis.

In some embodiments, a subject anti-SIRPα antibody is co-administered with (i.e., administered in combination with) an antibody that specifically binds a second antigen, e.g., a marker of a CD47-expressing cell (e.g., a cancer cell marker, a marker of an infected cell, etc.). In some embodiments, the second antigen is an antigen selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3). In some embodiments, a subject anti-SIRPα antibody is co-administered with (i.e., administered in combination with) one or more (e.g., 2 or more, 3 or more, etc.) antibodies that each specifically bind an antigen selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3). For example, in some cases, a subject anti-SIRPα antibody is co-administered with 1 or more antibodies selected from: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30), GEMTUZUMAB (binds CD33), LORVOTUZUMAB (binds CD56), IPILIMUMAB (binds CTLA-4 (CD152)), NIVOLUMAB (binds PD-1 (CD279)).

In some cases, a subject anti-SIRPα antibody that is administered to an individual is a multispecific antibody (e.g., a bispecific antibody). In some cases, the bispecific antibody specifically binds to SIRPα and a second antigen (e.g., a cancer cell marker). In some cases, the second antigen is selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3).

Therapeutic formulations comprising one or more antibodies of the disclosure are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD47 associated disease.

The therapeutic dose may be at least 0.01 mg/kg body weight, at least 0.05 mg/kg body weight; at least 0.1 mg/kg body weight, at least 0.5 mg/kg body weight, at least 1 mg/kg body weight, at least 2.5 mg/kg body weight, at least 5 mg/kg body weight, and not more than 300 mg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The anti-SIRPα antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-SIRPα antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the disclosure, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). An active agent in the composition can be the anti-SIRPα antibody. The label on, or associated with, the container can indicate that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

A subject anti-SIRPα antibody of the present disclosure can be provided in a kit, i.e., a packaged combination of reagents in predetermined amounts with instructions for administration and/or for performing an assay. In some cases, a subject kit can include one or more additional antibodies that can be used in combination with an anti-SIRPα antibody. For example, in some cases, a subject kit includes one or more antibodies that each binds a second antigen (e.g., a cancer cell marker). In some embodiments, the second antigen is an antigen selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3). In some embodiments, a subject kit includes a subject SIRPα antibody and one or more antibodies selected from: CETUXIMAB (binds EGFR), PANITUMUMAB (binds EGFR), RITUXIMAB (binds CD20), TRASTUZUMAB (binds HER2), PERTUZUMAB (binds HER2), ALEMTUZUMAB (binds CD52), and BRENTUXIMAB (binds CD30), GEMTUZUMAB (binds CD33), LORVOTUZUMAB (binds CD56), IPILIMUMAB (binds CTLA-4 (CD152)), and NIVOLUMAB (binds PD-1 (CD279)).

When the antibody is labeled with an enzyme, the kit can include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

KEY TO SEQUENCE LISTING

KWAR23 variable heavy chain (VH) (CDRs are underlined)
EVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSS (SEQ ID NO: 1)

CDRs of KWAR23 variable heavy chain (defined by IMGT)
CDR-H1: GFNIKDYY (SEQ ID NO: 2)

CDR-H2: IDPEDGET (SEQ ID NO: 3)

CDR-H3: ARWGAY (SEQ ID NO: 4)

KWAR23 variable light chain (VL) (CDRs are underlined)
QIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELK (SEQ ID NO: 5)

CDRs of KWAR23 variable light chain (defined by IMGT)
CDR-L1: SSVSSSY (SEQ ID NO: 6)

CDR-L2: STS (SEQ ID NO: 7)

CDR-L3: HQWSSYPRT (SEQ ID NO: 8)

Single-chain variable fragments (in Heavy-Light (HL) and Light-Heavy formats (LH)):
KWAR23 scFv HL (CDRs are underlined)
EVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSGGGGSGGGGSGGGGSQIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELK (SEQ ID NO: 9)

KWAR23 scFv LH (CDRs are underlined)
QIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELKRTTAASGSSGGSSSGAEVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVS (SEQ ID NO: 10)

Chimeric Fab (mouse variable domains, human IgG1 CH1, human kappa CL):
KWAR23 chiFab heavy chain (HC) (CDRs are underlined)
EVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC (SEQ ID NO: 11)

KWAR23 chiFab light chain (LC) (CDRs are underlined)
QIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 12)

Sequences of Bispecific Macrophage Enhancing antibodies (BiMEs):
Anti-CD20/Anti-SiRPα:
2B8_K23_DVD_VH (CDRs are underlined)
QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSSASTKGPEVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSS (SEQ ID NO: 13)

2B8_K23_DVD_VL (CDRs are underlined)
QIVLSQSPAILSASPGEKVTMTCRASSSVSYIHWFQQKPGSSPKPWIYATSNLASGVPVRFSGSGSGTSYSLTISRVEAEDAATYYCQQVVTSNPPTFGGGTKLEIKRTVAAPQIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELK (SEQ ID NO: 14)

Anti-HER2/Anti-SiRPα:
4D5_K23_DVD_VH (CDRs are underlined)
EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPEVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSS (SEQ ID NO: 15)

4D5_K23_DVD_VL (CDRs are underlined)
DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPQIVLTQSPAIMSASPGEKVTLTCSAS<u>SSVSSSY</u>LYWYQQKPGSSPKLWIY<u>STS</u>NLASGVPARFSGSGSGTSYSLTISSMEAEDAASYFC<u>HQWSSYPRT</u>FGAGTKLELK (SEQ ID NO: 16)

Anti-CD56/Anti-SiRPα:
56_K23_DVD_VH (CDRs are underlined)
QVQLVESGGGVVQPGRSLRLSCAASGFTFSSFGMHWVRQAPGKGLEWVAYISSGSFTIYYADSVKGRFTISRDNSKNTLYLQMNSLRAEDTAVYYCARMRKGYAMDYWGQGTLVTVSSASTKGPEVQLQQSGAELVKPGASVKLSCTA<u>SGFNIKDYY</u>IHWVQQRTEQGLEWIGR<u>IDPEDGET</u>KYAPKFQDKATITADTSSNTAYLHLSSLTSEDTAVYYC<u>ARWGAY</u>WGQGTLVTVSS (SEQ ID NO: 17)

56_K23_DVD_VL (CDRs are underlined)
DVVMTQSPLSLPVTLGQPASISCRSSQIIIHSDGNTYLEWFQQRPGQSPRRLIYKVSNRFSGVPDRFSGSGSGTDFTLKISRVEAEDVGVYYCFQGSHVPHTFGQGTKVEIKRTVAAPQIVLTQSPAIMSASPGEKVTLTCSAS<u>SSVSSS</u>YLYWYQQKPGSSPKLWIY<u>STS</u>NLASGVPARFSGSGSGTSYSLTISSMEAEDAASYFC<u>HQWSSYPRT</u>FGAGTKLELK (SEQ ID NO: 18)

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

Figure 8B:
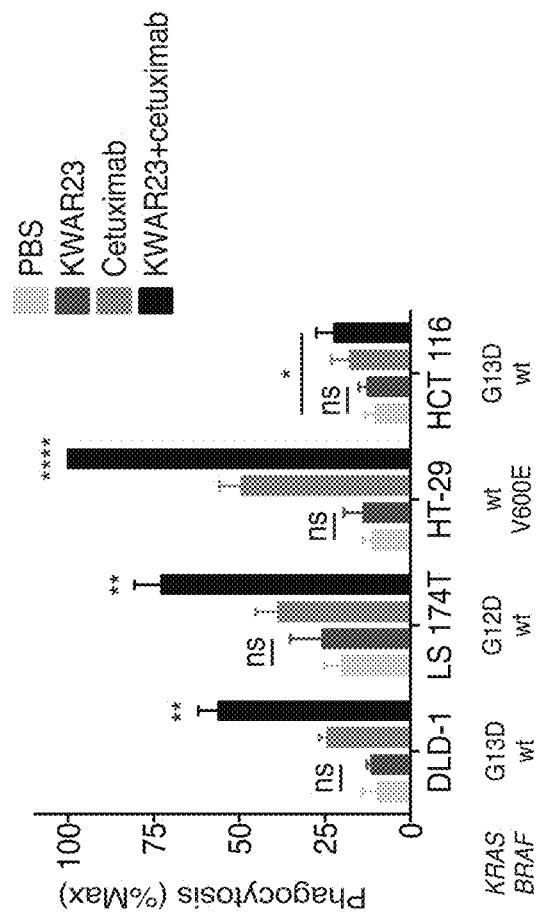
FIG. 8A-8B. KWAR23 enhances phagocytosis in response to cetuximab in the presence of downstream mutations in the EGFR signaling pathway.
Figure 8A:
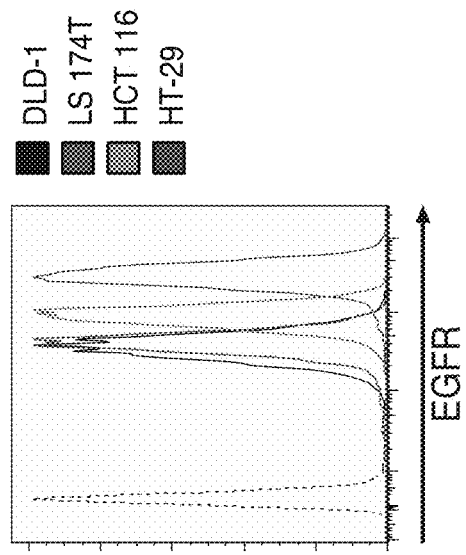

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

In order to construct Bispecific Macrophage Enhancing (BiME) antibodies, we first focused our efforts on obtaining a monoclonal anti-SIRPα antibody that blocks CD47 binding with high affinity. We recombinantly expressed the CD47-binding N-terminal IgV domain of human SIRPα (residues 1-118) in *E. coli* and immunized mice with the purified protein. Hybridomas were obtained and screened for SIRPα binding by ELISA. As an additional screening step, CD47-blocking was assessed through a cell-binding assay. Human THP-1 cells that express endogenous SIRPα were incubated with hybridoma supernatant and stained with fluorescent streptavidin tetramers conjugated to the biotinylated IgSF domain of human CD47. CD47 binding to the THP-1 cells was assessed by flow cytometry and clones that inhibited CD47 binding were further subcloned. The highest-expressing clone, KWAR23, was selected for further characterization.

We sought to approximate the affinity of KWAR23 for SIRPα and to determine if it potentiates phagocytosis of cancer cells. KWAR23 antibody was purified from hybridoma supernatant by protein G chromatography and titrated on THP-1 cells in the presence of 100 nM fluorescent CD47/streptavidin tetramers. As demonstrated in FIG. 1 KWAR23 potently inhibited CD47 binding with an $IC_{50}$ of ~270 pM.

The variable regions of KWAR23 were sequenced. To validate the sequences, KWAR23 scFvs were constructed using site overlap extension (SOE) PCR in two orientations: with an N-terminal light chain (LH scFv, see SEQ ID NO: 10) and conversely, with an N-terminal heavy-chain (HL scFv, see SEQ ID NO: 9). Both scFv's contained a 15-amino acid $(GGGGS)_3$ (SEQ ID NO: 19) linker between the variable fragments. The scFv's were then expressed as monomers in *E. coli*, yielding functional protein that inhibited CD47-binding to THP-1 cells with an $IC_{50}$ of ~35 nM (FIG. 1*a*). The difference in apparent affinity between intact KWAR23 and its scFv's is expected, as the antibody dimer provides avidity not enjoyed by the scFv monomers.

The functional efficacy of KWAR23 on tumor phagocytosis was assessed by a flow cytometry-based assay (FIG. 2). Briefly, GFP+ DLD-1 colon cancer cells, GFP+SK-BR-3 breast cancer cells, or GFP+ Raji lymphoma cells were co-cultured with primary human macrophages in the presence of a saturating concentration (10 μg/ml) of KWAR23 and varying concentrations of cetuximab (anti-EGFR), trastuzumab (anti-HER2), or rituximab (anti-CD20), respectively. Phagocytosis was assayed by determining the percentage of macrophages positive for GFP. Compared to vehicle (PBS), KWAR23 greatly increased both the potency (~10 fold lower $EC_{50}$) and efficacy (~50-100% higher $E_{max}$) of tumor cell phagocytosis induced by cetuximab, trastuzumab, or rituximab alone (FIG. 2).

The ability of KWAR23 to enhance the efficacy of particular antibody classes and/or isotypes was next assessed (FIG. 3). A variety of anti-CD20 classes and isotypes were tested, including: human IgG1, 2, 3, and 4; human IgM; human IgA1 and 2; human IgE; mouse IgG1 and 2a; and mouse IgA (FIG. 3A). The data show that KWAR23 enhanced the efficacy of all anti-CD20 IgG isotypes tested (both human and mouse), but did not significantly enhance the efficacy of anti-CD20 when the anti-CD20 was an IgM, IgA, or IgE. KWAR23 also enhanced the efficacy of anti-EGFR isotype IgG1 (cetuximab) and isotype IgG2 (panitumumab) demonstrating that the results are not specific to anti-CD20 (FIG. 3B). Thus, the data show that KWAR23 can enhance the efficacy of all IgG isotypes.

Based on the above data, multispecific antibodies are provided that can bind both SIRPα and a second antigen (e.g., a cancer marker such as CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, HAVCR2 (TIM3), and the like). FIG. 4A depicts a schematic of proposed activity of an exemplary subject bispecific antibody (also referred to as a Bispecific Macrophage Enhancing (BiME) antibody). FIG. 4B depicts a schematic of an exemplary anti-CD20 (and anti-SIRPα) BiME antibody. To demonstrate the efficacy of a subject bispecific antibody, phagocytosis was assayed when Raji lymphoma cells were contacted with a subject bispecific antibody in the presence of phagocytic cells (FIG. 4C). The bispecific antibody tested was a dual-variable-domain immunoglobulin (DVD-Ig) (with a heavy chain having the amino acid sequence set forth in SEQ ID NO: 13, and a light chain having the amino acid sequence set forth in SEQ ID NO: 14) that specifically binds SIRPα and CD20 (see FIG. 4B). The data demonstrate that the tested bispecific antibody exhibited greater efficacy when compared to using an anti-CD20 antibody (rituximab) alone (i.e., in the absence of a SIRPα binding reagent).

A bispecific antibody was generated with CD20 and the KWAR23 antibody. FIGS. 5A-5B show binding of the CD20 BiME to yeast expressing hSIRPα, as detected by an anti-human IgG4 Fc antibody conjugated to Alexa fluor-647 and an anti-rituximab antibody conjugated to FITC. Binding of KWAR23 to yeast expressing hSIRPα was detected by the anti-human IgG4 Fc antibody but not the anti-rituximab antibody.

Anti-SIRPα antibody (KWAR23) enhances ADCP and ADCC of cancer-targeting antibodies as shown in FIGS. 6A-E. Anti-SIRPα antibody (KWAR23) enhances antibody-dependent cellular phagocytosis (ADCP) of cancer-targeting antibodies by human macrophages: A. KWAR23+rituximab (anti-CD20) for human lymphoma cancer cells (Raji); B. KWAR23+trastuzumab (anti-Her2) for human breast cancer cells (SKBR3); C. KWAR23+vorsetuzumab (anti-CD70) for human renal cell cancer (RCC10, TK10, Caki1). Anti-SIRPα antibody (KWAR23) enhances antibody-dependent cellular cytotoxicty (ADCC) of cancer-targeting antibodies by human neutrophils: D. KWAR23+rituximab (anti-CD20) for human lymphoma cancer cells (Raji); E. KWAR23+trastuzumab (anti-Her2) for human breast cancer cells (SKBR3).

Bispecific macrophages enhancing antibodies (BiMEs) enhance ADCP and ADCC compared to the parental cancer-targeting antibodies as shown in FIGS. 7A-7E. Anti-SIRPα antibody (KWAR23) BiMEs enhance antibody-dependent cellular phagocytosis (ADCP) of cancer-targeting antibodies by human macrophages: A. Anti-CD20 BiME (KWAR23+rituximab (anti-CD20)) for human lymphoma cancer cells (Raji); B. Anti-Her2 BiME (KWAR23+trastuzumab (anti-Her2)) for human breast cancer cells (SKBR3); C. Anti-CD70 BiME (KWAR23+vorsetuzumab (anti-CD70)) for human renal cell cancer (RCC10, TK10, Caki1). Anti-SIRPα antibody (KWAR23) BiMEs enhance antibody-dependent cellular cytotoxicty (ADCC) of cancer-targeting antibodies by human neutrophils: D. Anti-CD20 BiME (KWAR23+rituximab (anti-CD20)) for human lymphoma cancer cells (Raji); E. Anti-Her2 BiME (KWAR23+trastuzumab (anti-Her2)) for human breast cancer cells (SKBR3).

KWAR23 enhances phagocytosis in response to cetuximab in the presence of downstream mutations in the EGFR signaling pathway, shown in FIG. 8. A. Expression of EGFR on the surface of human colon cancer cell lines as determined by binding of cetuximab. Dotted black line represents DLD-1 cells stained with isotype control antibody. B. Human macrophage phagocytosis of GFP+ colon cancer cell lines treated with the indicated therapies. Mutational status of KRAS and BRAF as previously reported. Data represent mean and standard deviation using macrophages from four independent blood donors. wt=wild-type; ns=not significant, *p<0.05, p<0.01, **p<0.0001 for KWAR23+cetuximab versus all other treatments or the indicated comparisons as assessed by two-way ANOVA with Sidak corrections for multiple comparisons.

Figure 9:
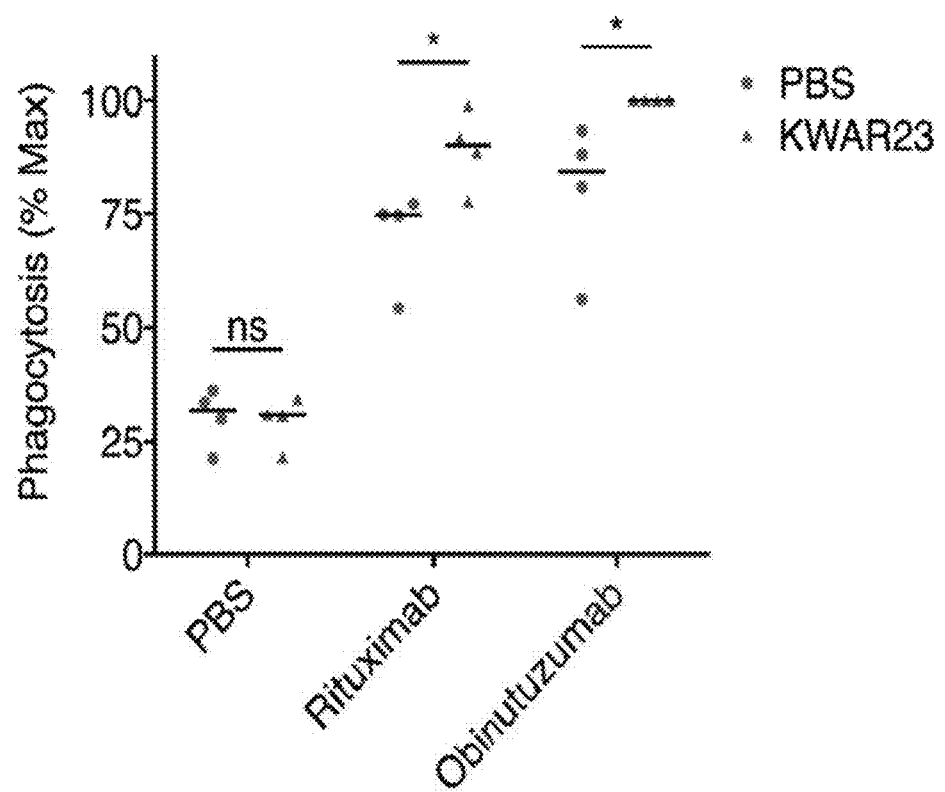
FIG. 9. KWAR23 enhances phagocytosis in response to glycoengineered antibodies. Human macrophage phagocytosis of Raji lymphoma cells in response to rituximab or the glycoengineered anti-CD20 antibody obinutuzumab. Points represent analysis using macrophages from independent blood donors, bars represent median across all donors. ns=not significant, $*p<0.05$ for the indicated comparisons by two-way ANOVA with Sidak corrections for multiple comparisons.

KWAR23 enhances phagocytosis in response to glycoengineered antibodies as shown in FIG. 9. Human macrophage phagocytosis of Raji lymphoma cells in response to rituximab or the glycoengineered anti-CD20 antibody obinutuzumab. Points represent analysis using macrophages from independent blood donors, bars represent median across all donors. ns=not significant, *p<0.05 for the indicated comparisons by two-way ANOVA with Sidak corrections for multiple comparisons.

That which is claimed is:

1. A method of inducing phagocytosis in an individual, the method comprising:
   administering to an individual a composition comprising a first antibody that specifically binds to human SIRPα but does not stimulate SIRPα signaling in a cell expressing the SIRPα, wherein the antibody comprises a heavy chain variable region comprising each of the CDR sequences set forth in SEQ ID NOs: 2-4, and a light chain variable region comprising each of the CDR sequences set forth in SEQ ID NOs: 6-8, and a second antibody that specifically binds a marker of a CD47-expressing cell;
   wherein said first and second antibodies are in a dose effective to induce phagocytosis.

2. The method of claim 1, wherein the first antibody comprises the amino acid sequence as set forth in any one of SEQ ID NOs: 9-10.

3. The method of claim 1, wherein the first antibody heavy chain comprises an amino acid sequence as set forth in any one of SEQ ID NOs: 1, 11, 13, 15, and 17.

4. The method of claim 1, wherein the first antibody light chain comprises an amino acid sequence as set forth in any one of SEQ ID NOs: 5, 12, 14, 16, and 18.

5. The method of claim 1, wherein the first antibody:
   (a) heavy chain comprises the amino acid sequence of SEQ ID NO: 1, and light chain comprises the amino acid sequence of SEQ ID NO: 5;
   (b) heavy chain comprises the amino acid sequence of SEQ ID NO: 11, and light chain comprises the amino acid sequence of SEQ ID NO: 12;
   (c) heavy chain comprises the amino acid sequence of SEQ ID NO: 13, and light chain comprises the amino acid sequence of SEQ ID NO: 14;
   (d) heavy chain comprises the amino acid sequence of SEQ ID NO: 15, and light chain comprises the amino acid sequence of SEQ ID NO: 16; or
   (e) heavy chain comprises the amino acid sequence of SEQ ID NO: 17, and the light chain comprises the amino acid sequence of SEQ ID NO: 18.

6. The method of claim 1, wherein the first antibody is a chimeric or humanized antibody.

7. The method of claim 1, wherein the first antibody is a humanized monoclonal antibody.

8. The method according to claim 1, wherein the individual is human.

9. The method according to claim 8, wherein the individual has a condition or disease selected from: cancer, a chronic infection, and an inflammatory disease.

10. The method according to claim 1, wherein the second antibody specifically binds a cancer cell marker.

11. The method according to claim 10, wherein the cancer cell marker is selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3).

12. A method of inducing phagocytosis in an individual, the method comprising:
    administering to the individual a composition comprising a bispecific antibody in a dose effective to induce phagocytosis, wherein the bispecific antibody comprises a first variable region that specifically binds to (i) human SIRPα but does not stimulate SIRPα signaling in a cell expressing the SIRPα, and (ii) a second variable region that specifically binds to a marker of a CD47-expressing cell;
    wherein the first variable region comprises a heavy chain region comprising each of the CDR sequences set forth in SEQ ID NOs: 2-4, and a light chain region comprising each of the CDR sequences set forth in SEQ ID NOs: 6-8.

13. The method of claim 12, wherein the second variable region binds an antigen selected from: CD19, CD20, CD22, CD24, CD25, CD30, CD33, CD38, CD44, CD52, CD56, CD70, CD96, CD97, CD99, CD123, CD279 (PD-1), EGFR, HER2, CD117, C-Met, PTHR2, and HAVCR2 (TIM3).

14. The method according to claim 9, wherein the cancer is selected from: a solid tumor, leukemia, and a lymphoma.

* * * * *

```
                       SEQUENCE LISTING

<160> NUMBER OF SEQ ID NOS: 19

<210> SEQ ID NO 1
<211> LENGTH: 113
<212> TYPE: PRT
<213> ORGANISM: Artificial sequence
<220> FEATURE:
<223> OTHER INFORMATION: Synthetic amino acid sequence

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser

<210> SEQ ID NO 2
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 2

Gly Phe Asn Ile Lys Asp Tyr Tyr
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 3

Ile Asp Pro Glu Asp Gly Glu Thr
1               5
```

```
<210> SEQ ID NO 4
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 4

Ala Arg Trp Gly Ala Tyr
1               5

<210> SEQ ID NO 5
<211> LENGTH: 108
<212> TYPE: PRT
<213> ORGANISM: Artificial sequence
<220> FEATURE:
<223> OTHER INFORMATION: Synthetic amino acid sequence

<400> SEQUENCE: 5

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys
            100                 105

<210> SEQ ID NO 6
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 6

Ser Ser Val Ser Ser Ser Tyr
1               5

<210> SEQ ID NO 7
<211> LENGTH: 3
<212> TYPE: PRT
<213> ORGANISM: Artificial sequence
<220> FEATURE:
<223> OTHER INFORMATION: Synthetic amino acid sequence

<400> SEQUENCE: 7

Ser Thr Ser
1

<210> SEQ ID NO 8
<211> LENGTH: 9
<212> TYPE: PRT
<213> ORGANISM: Artificial sequence
<220> FEATURE:
<223> OTHER INFORMATION: Synthetic amino acid sequence
```

```
<400> SEQUENCE: 8

His Gln Trp Ser Ser Tyr Pro Arg Thr
1               5

<210> SEQ ID NO 9
<211> LENGTH: 235
<212> TYPE: PRT
<213> ORGANISM: Artificial sequence
<220> FEATURE:
<223> OTHER INFORMATION: Synthetic amino acid sequence

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Gly Gly Gly Gly Ser Gly Gly Gly Ser Gly Gly Gly Gly Ser Gln
            115                 120                 125

Ile Val Leu Thr Gln Ser Pro Ala Ile Met Ser Ala Ser Pro Gly Glu
    130                 135                 140

Lys Val Thr Leu Thr Cys Ser Ala Ser Ser Ser Val Ser Ser Ser Tyr
145                 150                 155                 160

Leu Tyr Trp Tyr Gln Gln Lys Pro Gly Ser Ser Pro Lys Leu Trp Ile
                165                 170                 175

Tyr Ser Thr Ser Asn Leu Ala Ser Gly Val Pro Ala Arg Phe Ser Gly
            180                 185                 190

Ser Gly Ser Gly Thr Ser Tyr Ser Leu Thr Ile Ser Ser Met Glu Ala
        195                 200                 205

Glu Asp Ala Ala Ser Tyr Phe Cys His Gln Trp Ser Ser Tyr Pro Arg
    210                 215                 220

Thr Phe Gly Ala Gly Thr Lys Leu Glu Leu Lys
225                 230                 235

<210> SEQ ID NO 10
<211> LENGTH: 236
<212> TYPE: PRT
<213> ORGANISM: Artificial sequence
<220> FEATURE:
<223> OTHER INFORMATION: Synthetic amino acid sequence

<400> SEQUENCE: 10

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45
```

```
Ile Tyr Ser Thr Ser Asn Leu Ala Ser Gly Val Pro Ala Arg Phe Ser
    50                  55                  60
Gly Ser Gly Ser Gly Thr Ser Tyr Ser Leu Thr Ile Ser Ser Met Glu
 65                  70                  75                  80
Ala Glu Asp Ala Ala Ser Tyr Phe Cys His Gln Trp Ser Ser Tyr Pro
                 85                  90                  95
Arg Thr Phe Gly Ala Gly Thr Lys Leu Glu Leu Lys Gly Thr Thr Ala
            100                 105                 110
Ala Ser Gly Ser Ser Gly Gly Ser Ser Gly Ala Glu Val Gln Leu
            115                 120                 125
Gln Gln Ser Gly Ala Glu Leu Val Lys Pro Gly Ala Ser Val Lys Leu
130                 135                 140
Ser Cys Thr Ala Ser Gly Phe Asn Ile Lys Asp Tyr Tyr Ile His Trp
145                 150                 155                 160
Val Gln Gln Arg Thr Glu Gln Gly Leu Glu Trp Ile Gly Arg Ile Asp
                165                 170                 175
Pro Glu Asp Gly Glu Thr Lys Tyr Ala Pro Lys Phe Gln Asp Lys Ala
                180                 185                 190
Thr Ile Thr Ala Asp Thr Ser Ser Asn Thr Ala Tyr Leu His Leu Ser
                195                 200                 205
Ser Leu Thr Ser Glu Asp Thr Ala Val Tyr Tyr Cys Ala Arg Trp Gly
    210                 215                 220
Ala Tyr Trp Gly Gln Gly Thr Leu Val Thr Val Ser
225                 230                 235

<210> SEQ ID NO 11
<211> LENGTH: 216
<212> TYPE: PRT
<213> ORGANISM: Artificial sequence
<220> FEATURE:
<223> OTHER INFORMATION: Synthetic amino acid sequence

<400> SEQUENCE: 11

Glu Val Gln Leu Gln Gln Ser Gly Ala Glu Leu Val Lys Pro Gly Ala
  1               5                  10                  15
Ser Val Lys Leu Ser Cys Thr Ala Ser Gly Phe Asn Ile Lys Asp Tyr
             20                  25                  30
Tyr Ile His Trp Val Gln Gln Arg Thr Glu Gln Gly Leu Glu Trp Ile
             35                  40                  45
Gly Arg Ile Asp Pro Glu Asp Gly Glu Thr Lys Tyr Ala Pro Lys Phe
    50                  55                  60
Gln Asp Lys Ala Thr Ile Thr Ala Asp Thr Ser Ser Asn Thr Ala Tyr
 65                  70                  75                  80
Leu His Leu Ser Ser Leu Thr Ser Glu Asp Thr Ala Val Tyr Tyr Cys
                 85                  90                  95
Ala Arg Trp Gly Ala Tyr Trp Gly Gln Gly Thr Leu Val Thr Val Ser
            100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
            130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
```

```
Ser Leu Ser Ser Val Val Thr Val Pro Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 12
<211> LENGTH: 215
<212> TYPE: PRT
<213> ORGANISM: Artificial sequence
<220> FEATURE:
<223> OTHER INFORMATION: Synthetic amino acid sequence

<400> SEQUENCE: 12

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 13
<211> LENGTH: 240
<212> TYPE: PRT
<213> ORGANISM: Artificial sequence
<220> FEATURE:
<223> OTHER INFORMATION: Synthetic amino acid sequence

<400> SEQUENCE: 13

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45
```

Gly Ala Ile Tyr Pro Gly Asn Gly Asp Thr Ser Tyr Asn Gln Lys Phe
            50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ser Thr Lys Gly Pro Glu
            115                 120                 125

Val Gln Leu Gln Gln Ser Gly Ala Glu Leu Val Lys Pro Gly Ala Ser
130                 135                 140

Val Lys Leu Ser Cys Thr Ala Ser Gly Phe Asn Ile Lys Asp Tyr Tyr
145                 150                 155                 160

Ile His Trp Val Gln Gln Arg Thr Glu Gln Gly Leu Glu Trp Ile Gly
                165                 170                 175

Arg Ile Asp Pro Glu Asp Gly Glu Thr Lys Tyr Ala Pro Lys Phe Gln
            180                 185                 190

Asp Lys Ala Thr Ile Thr Ala Asp Thr Ser Ser Asn Thr Ala Tyr Leu
            195                 200                 205

His Leu Ser Ser Leu Thr Ser Glu Asp Thr Ala Val Tyr Tyr Cys Ala
            210                 215                 220

Arg Trp Gly Ala Tyr Trp Gly Gln Gly Thr Leu Val Thr Val Ser Ser
225                 230                 235                 240

<210> SEQ ID NO 14
<211> LENGTH: 220
<212> TYPE: PRT
<213> ORGANISM: Artificial sequence
<220> FEATURE:
<223> OTHER INFORMATION: Synthetic amino acid sequence

<400> SEQUENCE: 14

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Gln Ile Val Leu Thr Gln Ser Pro Ala Ile Met Ser Ala Ser Pro Gly
            115                 120                 125

Glu Lys Val Thr Leu Thr Cys Ser Ala Ser Ser Ser Val Ser Ser Ser
            130                 135                 140

Tyr Leu Tyr Trp Tyr Gln Gln Lys Pro Gly Ser Ser Pro Lys Leu Trp
145                 150                 155                 160

Ile Tyr Ser Thr Ser Asn Leu Ala Ser Gly Val Pro Ala Arg Phe Ser
                165                 170                 175

Gly Ser Gly Ser Gly Thr Ser Tyr Ser Leu Thr Ile Ser Ser Met Glu
            180                 185                 190

Ala Glu Asp Ala Ala Ser Tyr Phe Cys His Gln Trp Ser Ser Tyr Pro
        195                 200                 205

Arg Thr Phe Gly Ala Gly Thr Lys Leu Glu Leu Lys
    210                 215                 220

<210> SEQ ID NO 15
<211> LENGTH: 239
<212> TYPE: PRT
<213> ORGANISM: Artificial sequence
<220> FEATURE:
<223> OTHER INFORMATION: Synthetic amino acid sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Glu Val
        115                 120                 125

Gln Leu Gln Gln Ser Gly Ala Glu Leu Val Lys Pro Gly Ala Ser Val
    130                 135                 140

Lys Leu Ser Cys Thr Ala Ser Gly Phe Asn Ile Lys Asp Tyr Tyr Ile
145                 150                 155                 160

His Trp Val Gln Gln Arg Thr Glu Gln Gly Leu Glu Trp Ile Gly Arg
                165                 170                 175

Ile Asp Pro Glu Asp Gly Glu Thr Lys Tyr Ala Pro Lys Phe Gln Asp
            180                 185                 190

Lys Ala Thr Ile Thr Ala Asp Thr Ser Ser Asn Thr Ala Tyr Leu His
        195                 200                 205

Leu Ser Ser Leu Thr Ser Glu Asp Thr Ala Val Tyr Tyr Cys Ala Arg
    210                 215                 220

Trp Gly Ala Tyr Trp Gly Gln Gly Thr Leu Val Thr Val Ser Ser
225                 230                 235

<210> SEQ ID NO 16
<211> LENGTH: 221
<212> TYPE: PRT
<213> ORGANISM: Artificial sequence
<220> FEATURE:
<223> OTHER INFORMATION: Synthetic amino acid sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

```
Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                 100                 105                 110

Pro Gln Ile Val Leu Thr Gln Ser Pro Ala Ile Met Ser Ala Ser Pro
                 115                 120                 125

Gly Glu Lys Val Thr Leu Thr Cys Ser Ala Ser Ser Ser Val Ser Ser
 130                 135                 140

Ser Tyr Leu Tyr Trp Tyr Gln Gln Lys Pro Gly Ser Ser Pro Lys Leu
 145                 150                 155                 160

Trp Ile Tyr Ser Thr Ser Asn Leu Ala Ser Gly Val Pro Ala Arg Phe
                 165                 170                 175

Ser Gly Ser Gly Ser Gly Thr Ser Tyr Ser Leu Thr Ile Ser Ser Met
                 180                 185                 190

Glu Ala Glu Asp Ala Ala Ser Tyr Phe Cys His Gln Trp Ser Ser Tyr
                 195                 200                 205

Pro Arg Thr Phe Gly Ala Gly Thr Lys Leu Glu Leu Lys
                 210                 215                 220

<210> SEQ ID NO 17
<211> LENGTH: 237
<212> TYPE: PRT
<213> ORGANISM: Artificial sequence
<220> FEATURE:
<223> OTHER INFORMATION: Synthetic amino acid sequence

<400> SEQUENCE: 17

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Phe
                 20                  25                  30

Gly Met His Trp Val Arg Gln Ala Pro Gly Lys Gly Leu Glu Trp Val
         35                  40                  45

Ala Tyr Ile Ser Ser Gly Ser Phe Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Met Arg Lys Gly Tyr Ala Met Asp Tyr Trp Gly Gln Gly Thr
                 100                 105                 110

Leu Val Thr Val Ser Ser Ala Ser Thr Lys Gly Pro Glu Val Gln Leu
                 115                 120                 125

Gln Gln Ser Gly Ala Glu Leu Val Lys Pro Gly Ala Ser Val Lys Leu
 130                 135                 140

Ser Cys Thr Ala Ser Gly Phe Asn Ile Lys Asp Tyr Tyr Ile His Trp
 145                 150                 155                 160
```

```
Val Gln Gln Arg Thr Glu Gln Gly Leu Glu Trp Ile Gly Arg Ile Asp
            165                 170                 175

Pro Glu Asp Gly Glu Thr Lys Tyr Ala Pro Lys Phe Gln Asp Lys Ala
            180                 185                 190

Thr Ile Thr Ala Asp Thr Ser Ser Asn Thr Ala Tyr Leu His Leu Ser
            195                 200                 205

Ser Leu Thr Ser Glu Asp Thr Ala Val Tyr Tyr Cys Ala Arg Trp Gly
        210                 215                 220

Ala Tyr Trp Gly Gln Gly Thr Leu Val Thr Val Ser Ser
225                 230                 235

<210> SEQ ID NO 18
<211> LENGTH: 226
<212> TYPE: PRT
<213> ORGANISM: Artificial sequence
<220> FEATURE:
<223> OTHER INFORMATION: Synthetic amino acid sequence

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ile Ile Ile His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro His Thr Phe Gly Gln Gly Thr Lys Val Glu Ile Lys
            100                 105                 110

Arg Thr Val Ala Ala Pro Gln Ile Val Leu Thr Gln Ser Pro Ala Ile
        115                 120                 125

Met Ser Ala Ser Pro Gly Glu Lys Val Thr Leu Thr Cys Ser Ala Ser
    130                 135                 140

Ser Ser Val Ser Ser Tyr Leu Tyr Trp Tyr Gln Gln Lys Pro Gly
145                 150                 155                 160

Ser Ser Pro Lys Leu Trp Ile Tyr Ser Thr Ser Asn Leu Ala Ser Gly
                165                 170                 175

Val Pro Ala Arg Phe Ser Gly Ser Gly Ser Gly Thr Ser Tyr Ser Leu
            180                 185                 190

Thr Ile Ser Ser Met Glu Ala Glu Asp Ala Ala Ser Tyr Phe Cys His
        195                 200                 205

Gln Trp Ser Ser Tyr Pro Arg Thr Phe Gly Ala Gly Thr Lys Leu Glu
    210                 215                 220

Leu Lys
225

<210> SEQ ID NO 19
<211> LENGTH: 15
<212> TYPE: PRT
<213> ORGANISM: Artificial Sequence
<220> FEATURE:
<223> OTHER INFORMATION: Synthetic amino acid sequence
```

```
<400> SEQUENCE: 19

Gly Gly Gly Gly Ser Gly Gly Gly Gly Ser Gly Gly Gly Gly Ser
1               5                   10                  15
```